US008265724B2

(12) United States Patent
Petersen

(10) Patent No.: US 8,265,724 B2
(45) Date of Patent: Sep. 11, 2012

(54) CANCELLATION OF LIGHT SHUNTING

(75) Inventor: Ethan Petersen, Castro Valley, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1586 days.

(21) Appl. No.: 11/716,978

(22) Filed: Mar. 9, 2007

(65) Prior Publication Data

US 2008/0221427 A1 Sep. 11, 2008

(51) Int. Cl.
*A61B 5/1455* (2006.01)
(52) U.S. Cl. ......... 600/331; 600/310; 600/322; 600/323
(58) Field of Classification Search ............... 600/310, 600/316, 322–324, 331
See application file for complete search history.

(56) References Cited

U.S. PATENT DOCUMENTS

| 3,403,555 | A | 10/1968 | Versaci et al. |
|---|---|---|---|
| 3,536,545 | A | 10/1970 | Traynor et al. |
| D222,454 | S | 10/1971 | Beeber |
| 3,638,640 | A | 2/1972 | Shaw |
| 3,721,813 | A | 3/1973 | Condon et al. |
| 4,098,772 | A | 7/1978 | Bonk et al. |
| D250,275 | S | 11/1978 | Bond |
| D251,387 | S | 3/1979 | Ramsey et al. |
| D262,488 | S | 12/1981 | Rossman et al. |
| 4,334,544 | A | 6/1982 | Hill et al. |
| 4,350,165 | A | 9/1982 | Striese |
| 4,353,372 | A | 10/1982 | Ayer |
| 4,380,240 | A | 4/1983 | Jobsis et al. |
| 4,406,289 | A | 9/1983 | Wesseling et al. |
| 4,510,551 | A | 4/1985 | Brainard, II |
| 4,586,513 | A | 5/1986 | Hamaguri |
| 4,603,700 | A | 8/1986 | Nichols et al. |
| 4,621,643 | A | 11/1986 | New, Jr. et al. |
| 4,653,498 | A | 3/1987 | New, Jr. et al. |
| 4,677,528 | A | 6/1987 | Miniet |
| 4,685,464 | A | 8/1987 | Goldberger et al. |
| 4,694,833 | A | 9/1987 | Hamaguri |
| 4,697,593 | A | 10/1987 | Evans et al. |
| 4,700,708 | A | 10/1987 | New, Jr. et al. |
| 4,714,080 | A | 12/1987 | Edgar, Jr. et al. |
| 4,714,341 | A | 12/1987 | Hamaguri et al. |

(Continued)

FOREIGN PATENT DOCUMENTS

CN 1540314 A 10/2004

(Continued)

OTHER PUBLICATIONS

Lee, Jason C.S., et al., "Measurement of Percent Carboxyhemoglobin with Pulse-Oximetry Technique," *IEEE Engineering in Medicine & Biology Society 10th Annual International Conference*, CH2566-88, vol. 88, pp. 1781-1782 (1988).

(Continued)

*Primary Examiner* — Eric Winakur
*Assistant Examiner* — Chu Chuan (JJ) Liu
(74) *Attorney, Agent, or Firm* — Fletcher Yoder

(57) ABSTRACT

There is provided a system and method for canceling shunted light. The method includes transmitting electromagnetic radiation at tissue of interest and generating a signal representative of detected electromagnetic radiation. A portion of the generated signal representing shunted light is canceled from the generated signal and the remaining portion of the generated signal is used to compute physiological parameters.

14 Claims, 4 Drawing Sheets

U.S. PATENT DOCUMENTS

| | | |
|---|---|---|
| 4,722,120 A | 2/1988 | Lu |
| 4,726,382 A | 2/1988 | Boehmer et al. |
| 4,759,369 A | 7/1988 | Taylor |
| 4,770,179 A | 9/1988 | New, Jr. et al. |
| 4,773,422 A | 9/1988 | Isaacson et al. |
| 4,776,339 A | 10/1988 | Schreiber |
| 4,781,195 A | 11/1988 | Martin |
| 4,783,815 A | 11/1988 | Buttner |
| 4,796,636 A | 1/1989 | Branstetter et al. |
| 4,800,495 A | 1/1989 | Smith |
| 4,800,885 A | 1/1989 | Johnson |
| 4,802,486 A | 2/1989 | Goodman et al. |
| 4,805,623 A | 2/1989 | Jöbsis |
| 4,807,630 A | 2/1989 | Malinouskas |
| 4,807,631 A | 2/1989 | Hersh et al. |
| 4,819,646 A | 4/1989 | Cheung et al. |
| 4,819,752 A | 4/1989 | Zelin |
| 4,824,242 A | 4/1989 | Frick et al. |
| 4,825,872 A | 5/1989 | Tan et al. |
| 4,825,879 A | 5/1989 | Tan et al. |
| 4,830,014 A | 5/1989 | Goodman et al. |
| 4,832,484 A | 5/1989 | Aoyagi et al. |
| 4,846,183 A | 7/1989 | Martin |
| 4,848,901 A | 7/1989 | Hood, Jr. |
| 4,854,699 A | 8/1989 | Edgar, Jr. |
| 4,859,056 A | 8/1989 | Prosser et al. |
| 4,859,057 A | 8/1989 | Taylor et al. |
| 4,863,265 A | 9/1989 | Flower et al. |
| 4,865,038 A | 9/1989 | Rich et al. |
| 4,867,557 A | 9/1989 | Takatani et al. |
| 4,869,253 A | 9/1989 | Craig, Jr. et al. |
| 4,869,254 A | 9/1989 | Stone et al. |
| 4,880,304 A | 11/1989 | Jaeb et al. |
| 4,883,055 A | 11/1989 | Merrick |
| 4,883,353 A | 11/1989 | Hansmann et al. |
| 4,890,619 A | 1/1990 | Hatschek |
| 4,892,101 A | 1/1990 | Cheung et al. |
| 4,901,238 A | 2/1990 | Suzuki et al. |
| 4,908,762 A | 3/1990 | Suzuki et al. |
| 4,911,167 A | 3/1990 | Corenman et al. |
| 4,913,150 A | 4/1990 | Cheung et al. |
| 4,926,867 A | 5/1990 | Kanda et al. |
| 4,927,264 A | 5/1990 | Shiga et al. |
| 4,928,692 A | 5/1990 | Goodman et al. |
| 4,934,372 A | 6/1990 | Corenman et al. |
| 4,936,679 A | 6/1990 | Mersch |
| 4,938,218 A | 7/1990 | Goodman et al. |
| 4,942,877 A | 7/1990 | Sakai et al. |
| 4,948,248 A | 8/1990 | Lehman |
| 4,955,379 A | 9/1990 | Hall |
| 4,960,126 A | 10/1990 | Conlon et al. |
| 4,964,408 A | 10/1990 | Hink et al. |
| 4,971,062 A | 11/1990 | Hasebe et al. |
| 4,972,331 A | 11/1990 | Chance |
| 4,974,591 A | 12/1990 | Awazu et al. |
| 5,007,423 A | 4/1991 | Branstetter et al. |
| 5,025,791 A | 6/1991 | Niwa |
| RE33,643 E | 7/1991 | Isaacson et al. |
| 5,028,787 A | 7/1991 | Rosenthal et al. |
| 5,035,243 A | 7/1991 | Muz |
| 5,040,539 A | 8/1991 | Schmitt et al. |
| 5,041,187 A | 8/1991 | Hink et al. |
| 5,054,488 A | 10/1991 | Muz |
| 5,055,671 A | 10/1991 | Jones |
| 5,058,588 A | 10/1991 | Kaestle |
| 5,065,749 A | 11/1991 | Hasebe et al. |
| 5,066,859 A | 11/1991 | Karkar et al. |
| 5,069,213 A | 12/1991 | Polczynski |
| 5,078,136 A | 1/1992 | Stone et al. |
| 5,086,229 A | 2/1992 | Rosenthal et al. |
| 5,088,493 A | 2/1992 | Giannini et al. |
| 5,090,410 A | 2/1992 | Saper et al. |
| 5,094,239 A | 3/1992 | Jaeb et al. |
| 5,094,240 A | 3/1992 | Muz |
| 5,099,841 A | 3/1992 | Heinonen et al. |
| 5,099,842 A | 3/1992 | Mannheimer et al. |
| H1039 H | 4/1992 | Tripp et al. |
| 5,104,623 A | 4/1992 | Miller |
| 5,109,849 A | 5/1992 | Goodman et al. |
| 5,111,817 A | 5/1992 | Clark et al. |
| 5,113,861 A | 5/1992 | Rother |
| D326,715 S | 6/1992 | Schmidt |
| 5,119,815 A | 6/1992 | Chance |
| 5,122,974 A | 6/1992 | Chance |
| 5,125,403 A | 6/1992 | Culp |
| 5,127,406 A | 7/1992 | Yamaguchi |
| 5,131,391 A | 7/1992 | Sakai et al. |
| 5,140,989 A | 8/1992 | Lewis et al. |
| 5,152,296 A | 10/1992 | Simons |
| 5,154,175 A | 10/1992 | Gunther |
| 5,158,082 A | 10/1992 | Jones |
| 5,167,230 A | 12/1992 | Chance |
| 5,170,786 A | 12/1992 | Thomas et al. |
| 5,188,108 A | 2/1993 | Secker et al. |
| 5,190,038 A | 3/1993 | Polson et al. |
| 5,193,542 A | 3/1993 | Missanelli et al. |
| 5,193,543 A | 3/1993 | Yelderman |
| 5,203,329 A | 4/1993 | Takatani et al. |
| 5,209,230 A | 5/1993 | Swedlow et al. |
| 5,213,099 A | 5/1993 | Tripp et al. |
| 5,216,598 A | 6/1993 | Branstetter et al. |
| 5,217,012 A | 6/1993 | Young et al. |
| 5,217,013 A | 6/1993 | Lewis et al. |
| 5,218,207 A | 6/1993 | Rosenthal |
| 5,218,962 A | 6/1993 | Mannheimer et al. |
| 5,224,478 A | 7/1993 | Sakai et al. |
| 5,226,417 A | 7/1993 | Swedlow et al. |
| 5,228,440 A | 7/1993 | Chung et al. |
| 5,237,994 A | 8/1993 | Goldberger |
| 5,239,185 A | 8/1993 | Ito et al. |
| 5,246,002 A | 9/1993 | Prosser |
| 5,246,003 A | 9/1993 | DeLonzor |
| 5,247,931 A | 9/1993 | Norwood |
| 5,247,932 A | 9/1993 | Chung et al. |
| 5,249,576 A | 10/1993 | Goldberger et al. |
| 5,253,645 A | 10/1993 | Freidman et al. |
| 5,253,646 A | 10/1993 | Delpy et al. |
| 5,259,381 A | 11/1993 | Cheung et al. |
| 5,259,761 A | 11/1993 | Schnettler et al. |
| 5,263,244 A | 11/1993 | Centa et al. |
| 5,267,562 A | 12/1993 | Ukawa et al. |
| 5,267,563 A | 12/1993 | Swedlow et al. |
| 5,267,566 A | 12/1993 | Choucair et al. |
| 5,273,036 A | 12/1993 | Kronberg et al. |
| 5,275,159 A | 1/1994 | Griebel |
| 5,278,627 A | 1/1994 | Aoyagi et al. |
| 5,279,295 A | 1/1994 | Martens et al. |
| 5,285,783 A | 2/1994 | Secker |
| 5,285,784 A | 2/1994 | Seeker |
| 5,287,853 A | 2/1994 | Vester et al. |
| 5,291,884 A | 3/1994 | Heinemann et al. |
| 5,297,548 A | 3/1994 | Pologe |
| 5,299,120 A | 3/1994 | Kaestle |
| 5,299,570 A | 4/1994 | Hatschek |
| 5,309,908 A | 5/1994 | Freidman et al. |
| 5,311,865 A | 5/1994 | Mayeux |
| 5,313,940 A | 5/1994 | Fuse et al. |
| 5,323,776 A | 6/1994 | Blakely et al. |
| 5,329,922 A | 7/1994 | Atlee, III |
| 5,337,744 A | 8/1994 | Branigan |
| 5,337,745 A | 8/1994 | Benaron |
| 5,339,810 A | 8/1994 | Ivers et al. |
| 5,343,818 A | 9/1994 | McCarthy et al. |
| 5,343,869 A | 9/1994 | Pross et al. |
| 5,348,003 A | 9/1994 | Caro |
| 5,348,004 A | 9/1994 | Hollub et al. |
| 5,348,005 A | 9/1994 | Merrick |
| 5,349,519 A | 9/1994 | Kaestle |
| 5,349,952 A | 9/1994 | McCarthy et al. |
| 5,349,953 A | 9/1994 | McCarthy et al. |
| 5,351,685 A | 10/1994 | Potratz |
| 5,353,799 A | 10/1994 | Chance |
| 5,355,880 A | 10/1994 | Thomas et al. |
| 5,355,882 A | 10/1994 | Ukawa et al. |
| 5,361,758 A | 11/1994 | Hall et al. |
| 5,365,066 A | 11/1994 | Krueger, Jr. et al. |
| 5,368,025 A | 11/1994 | Young et al. |

| Patent | Date | Inventor |
|---|---|---|
| 5,368,026 A | 11/1994 | Swedlow et al. |
| 5,368,224 A | 11/1994 | Richardson et al. |
| 5,372,136 A | 12/1994 | Steuer et al. |
| 5,377,675 A | 1/1995 | Ruskewicz et al. |
| 5,385,143 A | 1/1995 | Aoyagi |
| 5,387,122 A | 2/1995 | Goldberger et al. |
| 5,390,670 A | 2/1995 | Centa et al. |
| 5,392,777 A | 2/1995 | Swedlow et al. |
| 5,398,680 A | 3/1995 | Polson et al. |
| 5,402,777 A | 4/1995 | Warring et al. |
| 5,402,779 A | 4/1995 | Chen et al. |
| 5,411,023 A | 5/1995 | Morris, Sr. et al. |
| 5,411,024 A | 5/1995 | Thomas et al. |
| 5,413,099 A | 5/1995 | Schmidt et al. |
| 5,413,100 A | 5/1995 | Barthelemy et al. |
| 5,413,101 A | 5/1995 | Sugiura |
| 5,413,102 A | 5/1995 | Schmidt et al. |
| 5,417,207 A | 5/1995 | Young et al. |
| 5,421,329 A | 6/1995 | Casciani et al. |
| 5,425,360 A | 6/1995 | Nelson |
| 5,425,362 A | 6/1995 | Siker et al. |
| 5,427,093 A | 6/1995 | Ogawa et al. |
| 5,429,128 A | 7/1995 | Cadell et al. |
| 5,429,129 A | 7/1995 | Lovejoy et al. |
| 5,431,159 A | 7/1995 | Baker et al. |
| 5,431,170 A | 7/1995 | Mathews |
| 5,437,275 A | 8/1995 | Amundsen et al. |
| 5,438,986 A | 8/1995 | Disch et al. |
| 5,448,991 A | 9/1995 | Polson et al. |
| 5,452,717 A | 9/1995 | Branigan et al. |
| 5,465,714 A | 11/1995 | Scheuing |
| 5,469,845 A | 11/1995 | DeLonzor et al. |
| RE35,122 E | 12/1995 | Corenman et al. |
| 5,482,034 A | 1/1996 | Lewis et al. |
| 5,482,036 A | 1/1996 | Diab et al. |
| 5,485,847 A | 1/1996 | Baker, Jr. |
| 5,490,505 A | 2/1996 | Diab et al. |
| 5,490,523 A | 2/1996 | Isaacson et al. |
| 5,491,299 A | 2/1996 | Naylor et al. |
| 5,494,032 A | 2/1996 | Robinson et al. |
| 5,494,043 A | 2/1996 | O'Sullivan et al. |
| 5,497,771 A | 3/1996 | Rosenheimer |
| 5,499,627 A | 3/1996 | Steuer et al. |
| 5,503,148 A | 4/1996 | Pologe et al. |
| 5,505,199 A | 4/1996 | Kim |
| 5,507,286 A | 4/1996 | Solenberger |
| 5,511,546 A | 4/1996 | Hon |
| 5,517,988 A | 5/1996 | Gerhard |
| 5,520,177 A | 5/1996 | Ogawa et al. |
| 5,521,851 A | 5/1996 | Wei et al. |
| 5,522,388 A | 6/1996 | Ishikawa et al. |
| 5,524,617 A | 6/1996 | Mannheimer |
| 5,529,064 A | 6/1996 | Rall et al. |
| 5,533,507 A | 7/1996 | Potratz et al. |
| 5,551,423 A | 9/1996 | Sugiura |
| 5,551,424 A | 9/1996 | Morrison et al. |
| 5,553,614 A | 9/1996 | Chance |
| 5,553,615 A | 9/1996 | Carim et al. |
| 5,555,882 A | 9/1996 | Richardson et al. |
| 5,558,096 A | 9/1996 | Palatnik |
| 5,560,355 A | 10/1996 | Merchant et al. |
| 5,564,417 A | 10/1996 | Chance |
| 5,575,284 A | 11/1996 | Athan et al. |
| 5,575,285 A | 11/1996 | Takanashi et al. |
| 5,577,500 A | 11/1996 | Potratz |
| 5,582,169 A | 12/1996 | Oda et al. |
| 5,584,296 A | 12/1996 | Cui et al. |
| 5,588,425 A | 12/1996 | Sackner et al. |
| 5,588,427 A | 12/1996 | Tien |
| 5,590,652 A | 1/1997 | Inai |
| 5,595,176 A | 1/1997 | Yamaura |
| 5,596,986 A | 1/1997 | Goldfarb |
| 5,611,337 A | 3/1997 | Bukta |
| 5,617,852 A | 4/1997 | MacGregor |
| 5,619,992 A | 4/1997 | Guthrie et al. |
| 5,626,140 A | 5/1997 | Feldman et al. |
| 5,630,413 A | 5/1997 | Thomas et al. |
| 5,632,272 A | 5/1997 | Diab et al. |
| 5,632,273 A | 5/1997 | Suzuki |
| 5,634,459 A | 6/1997 | Gardosi |
| 5,638,593 A | 6/1997 | Gerhardt et al. |
| 5,638,816 A | 6/1997 | Kiani-Azarbayjany et al. |
| 5,638,818 A | 6/1997 | Diab et al. |
| 5,645,059 A | 7/1997 | Fein et al. |
| 5,645,060 A | 7/1997 | Yorkey |
| 5,645,440 A | 7/1997 | Tobler et al. |
| 5,660,567 A | 8/1997 | Nierlich et al. |
| 5,662,105 A | 9/1997 | Tien |
| 5,662,106 A | 9/1997 | Swedlow et al. |
| 5,664,270 A | 9/1997 | Bell et al. |
| 5,666,952 A | 9/1997 | Fuse et al. |
| 5,671,529 A | 9/1997 | Nelson |
| 5,673,692 A | 10/1997 | Schulze et al. |
| 5,673,693 A | 10/1997 | Solenberger |
| 5,676,139 A | 10/1997 | Goldberger et al. |
| 5,676,141 A | 10/1997 | Hollub |
| 5,678,544 A | 10/1997 | DeLonzor et al. |
| 5,680,857 A | 10/1997 | Pelikan et al. |
| 5,685,299 A | 11/1997 | Diab et al. |
| 5,685,301 A | 11/1997 | Klomhaus |
| 5,687,719 A | 11/1997 | Sato et al. |
| 5,687,722 A | 11/1997 | Tien et al. |
| 5,692,503 A | 12/1997 | Keunstner |
| 5,692,505 A | 12/1997 | Fouts |
| 5,709,205 A | 1/1998 | Bukta |
| 5,713,355 A | 2/1998 | Richardson et al. |
| 5,724,967 A | 3/1998 | Venkatachalam |
| 5,727,547 A | 3/1998 | Levinson et al. |
| 5,730,124 A | 3/1998 | Yamauchi |
| 5,731,582 A | 3/1998 | West |
| D393,830 S | 4/1998 | Tobler et al. |
| 5,743,260 A | 4/1998 | Chung et al. |
| 5,743,262 A | 4/1998 | Lepper, Jr. et al. |
| 5,743,263 A | 4/1998 | Baker, Jr. |
| 5,746,206 A | 5/1998 | Mannheimer |
| 5,746,697 A | 5/1998 | Swedlow et al. |
| 5,752,914 A | 5/1998 | DeLonzor et al. |
| 5,755,226 A | 5/1998 | Carim et al. |
| 5,758,644 A | 6/1998 | Diab et al. |
| 5,760,910 A | 6/1998 | Lepper, Jr. et al. |
| 5,766,125 A | 6/1998 | Aoyagi et al. |
| 5,766,127 A | 6/1998 | Pologe et al. |
| 5,769,785 A | 6/1998 | Diab et al. |
| 5,772,587 A | 6/1998 | Gratton et al. |
| 5,774,213 A | 6/1998 | Trebino et al. |
| 5,776,058 A | 7/1998 | Levinson et al. |
| 5,776,059 A | 7/1998 | Kaestle |
| 5,779,630 A | 7/1998 | Fein et al. |
| 5,779,631 A | 7/1998 | Chance |
| 5,782,237 A | 7/1998 | Casciani et al. |
| 5,782,756 A | 7/1998 | Mannheimer |
| 5,782,757 A | 7/1998 | Diab et al. |
| 5,782,758 A | 7/1998 | Ausec et al. |
| 5,783,821 A | 7/1998 | Costello, Jr. |
| 5,786,592 A | 7/1998 | Hök |
| 5,788,634 A | 8/1998 | Suda et al. |
| 5,790,729 A | 8/1998 | Pologe et al. |
| 5,792,052 A | 8/1998 | Isaacson et al. |
| 5,795,292 A | 8/1998 | Lewis et al. |
| 5,797,841 A | 8/1998 | DeLonzor et al. |
| 5,800,348 A | 9/1998 | Kaestle |
| 5,800,349 A | 9/1998 | Isaacson et al. |
| 5,803,908 A | 9/1998 | Steuer et al. |
| 5,803,910 A | 9/1998 | Potratz |
| 5,807,246 A | 9/1998 | Sakaguchi et al. |
| 5,807,247 A | 9/1998 | Merchant et al. |
| 5,807,248 A | 9/1998 | Mills |
| 5,810,723 A | 9/1998 | Aldrich |
| 5,810,724 A | 9/1998 | Gronvall |
| 5,813,980 A | 9/1998 | Levinson et al. |
| 5,817,008 A | 10/1998 | Rafert et al. |
| 5,817,009 A | 10/1998 | Rosenheimer et al. |
| 5,817,010 A | 10/1998 | Hibl |
| 5,818,985 A | 10/1998 | Merchant et al. |
| 5,820,550 A | 10/1998 | Polson et al. |
| 5,823,950 A | 10/1998 | Diab et al. |
| 5,823,952 A | 10/1998 | Levinson et al. |
| 5,827,179 A | 10/1998 | Lichter et al. |

| Patent | Date | Inventors |
|---|---|---|
| 5,827,182 A | 10/1998 | Raley et al. |
| 5,829,439 A | 11/1998 | Yokosawa et al. |
| 5,830,135 A | 11/1998 | Bosque et al. |
| 5,830,136 A | 11/1998 | DeLonzor et al. |
| 5,830,137 A | 11/1998 | Scharf |
| 5,830,139 A | 11/1998 | Abreu |
| 5,839,439 A | 11/1998 | Nierlich et al. |
| RE36,000 E | 12/1998 | Swedlow et al. |
| 5,842,979 A | 12/1998 | Jarman et al. |
| 5,842,981 A | 12/1998 | Larsen et al. |
| 5,842,982 A | 12/1998 | Mannheimer |
| 5,846,190 A | 12/1998 | Woehrle |
| 5,851,178 A | 12/1998 | Aronow |
| 5,851,179 A | 12/1998 | Ritson et al. |
| 5,853,364 A | 12/1998 | Baker, Jr. et al. |
| 5,860,919 A | 1/1999 | Kiani-Azarbayjany et al. |
| 5,865,736 A | 2/1999 | Baker, Jr. et al. |
| 5,873,821 A | 2/1999 | Chance et al. |
| 5,879,294 A | 3/1999 | Anderson et al. |
| 5,885,213 A | 3/1999 | Richardson et al. |
| 5,890,929 A | 4/1999 | Mills et al. |
| 5,891,021 A | 4/1999 | Dillon et al. |
| 5,891,022 A | 4/1999 | Pologe |
| 5,891,024 A | 4/1999 | Jarman et al. |
| 5,891,025 A | 4/1999 | Buschmann et al. |
| 5,891,026 A | 4/1999 | Wang et al. |
| 5,902,235 A | 5/1999 | Lewis et al. |
| 5,910,108 A | 6/1999 | Solenberger |
| 5,911,690 A | 6/1999 | Rall |
| 5,912,656 A | 6/1999 | Tham et al. |
| 5,913,819 A | 6/1999 | Taylor et al. |
| 5,916,154 A | 6/1999 | Hobbs et al. |
| 5,916,155 A | 6/1999 | Levinson et al. |
| 5,919,133 A | 7/1999 | Taylor et al. |
| 5,919,134 A | 7/1999 | Diab |
| 5,920,263 A | 7/1999 | Huttenhoff et al. |
| 5,921,921 A | 7/1999 | Potratz et al. |
| 5,922,607 A | 7/1999 | Bernreuter |
| 5,924,979 A | 7/1999 | Swedlow et al. |
| 5,924,980 A | 7/1999 | Coetzee |
| 5,924,982 A | 7/1999 | Chin |
| 5,924,985 A | 7/1999 | Jones |
| 5,934,277 A | 8/1999 | Mortz |
| 5,934,925 A | 8/1999 | Tobler et al. |
| 5,940,182 A | 8/1999 | Lepper, Jr. et al. |
| 5,954,644 A | 9/1999 | Dettling et al. |
| 5,957,840 A | 9/1999 | Terasawa et al. |
| 5,960,610 A | 10/1999 | Levinson et al. |
| 5,961,450 A | 10/1999 | Merchant et al. |
| 5,961,452 A | 10/1999 | Chung et al. |
| 5,964,701 A | 10/1999 | Asada et al. |
| 5,971,930 A | 10/1999 | Elghazzawi |
| 5,978,691 A | 11/1999 | Mills |
| 5,978,693 A | 11/1999 | Hamilton et al. |
| 5,983,120 A | 11/1999 | Groner et al. |
| 5,983,122 A | 11/1999 | Jarman et al. |
| 5,987,343 A | 11/1999 | Kinast |
| 5,991,648 A | 11/1999 | Levin |
| 5,995,855 A | 11/1999 | Kiani et al. |
| 5,995,856 A | 11/1999 | Mannheimer et al. |
| 5,995,858 A | 11/1999 | Kinast |
| 5,995,859 A | 11/1999 | Takahashi |
| 5,997,343 A | 12/1999 | Mills et al. |
| 5,999,834 A | 12/1999 | Wang et al. |
| 6,002,952 A | 12/1999 | Diab et al. |
| 6,005,658 A | 12/1999 | Kaluza et al. |
| 6,006,120 A | 12/1999 | Levin |
| 6,011,985 A | 1/2000 | Athan et al. |
| 6,011,986 A | 1/2000 | Diab et al. |
| 6,014,576 A | 1/2000 | Raley et al. |
| 6,018,673 A | 1/2000 | Chin et al. |
| 6,018,674 A | 1/2000 | Aronow |
| 6,022,321 A | 2/2000 | Amano et al. |
| 6,023,541 A | 2/2000 | Merchant et al. |
| 6,026,312 A | 2/2000 | Shemwell et al. |
| 6,026,314 A | 2/2000 | Amerov et al. |
| 6,031,603 A | 2/2000 | Fine et al. |
| 6,035,223 A | 3/2000 | Baker, Jr. |
| 6,036,642 A | 3/2000 | Diab et al. |
| 6,041,247 A | 3/2000 | Weckstrom et al. |
| 6,044,283 A | 3/2000 | Fein et al. |
| 6,047,201 A | 4/2000 | Jackson, III |
| 6,055,447 A | 4/2000 | Weil |
| 6,061,584 A | 5/2000 | Lovejoy et al. |
| 6,064,898 A | 5/2000 | Aldrich |
| 6,064,899 A | 5/2000 | Fein et al. |
| 6,067,462 A | 5/2000 | Diab et al. |
| 6,073,038 A | 6/2000 | Wang et al. |
| 6,078,829 A | 6/2000 | Uchida |
| 6,078,833 A | 6/2000 | Hueber |
| 6,081,735 A | 6/2000 | Diab et al. |
| 6,083,157 A | 7/2000 | Noller |
| 6,083,172 A | 7/2000 | Baker, Jr. et al. |
| 6,088,607 A | 7/2000 | Diab et al. |
| 6,094,592 A | 7/2000 | Yorkey et al. |
| 6,095,974 A | 8/2000 | Shemwell et al. |
| 6,104,938 A | 8/2000 | Huiku et al. |
| 6,104,939 A | 8/2000 | Groner |
| 6,112,107 A | 8/2000 | Hannula |
| 6,113,541 A | 9/2000 | Dias et al. |
| 6,115,621 A | 9/2000 | Chin |
| 6,120,460 A | 9/2000 | Abreu |
| 6,122,535 A | 9/2000 | Kaestle et al. |
| 6,133,994 A | 10/2000 | Mathews et al. |
| 6,134,460 A | 10/2000 | Chance |
| 6,135,952 A | 10/2000 | Coetzee |
| 6,144,444 A | 11/2000 | Haworth et al. |
| 6,144,867 A | 11/2000 | Walker et al. |
| 6,144,868 A | 11/2000 | Parker |
| 6,149,481 A | 11/2000 | Wang et al. |
| 6,151,107 A | 11/2000 | Schöllermann et al. |
| 6,151,516 A | 11/2000 | Kiani-Azarbayjani et al. |
| 6,151,518 A | 11/2000 | Hayashi |
| 6,152,754 A | 11/2000 | Gerhardt et al. |
| 6,154,667 A | 11/2000 | Miura et al. |
| 6,157,850 A | 12/2000 | Diab et al. |
| 6,159,147 A | 12/2000 | Lichter |
| 6,163,715 A | 12/2000 | Larsen et al. |
| 6,165,005 A | 12/2000 | Mills et al. |
| 6,173,196 B1 | 1/2001 | Delonzor et al. |
| 6,178,343 B1 | 1/2001 | Bindszus et al. |
| 6,179,159 B1 | 1/2001 | Gurley |
| 6,181,958 B1 | 1/2001 | Steuer et al. |
| 6,181,959 B1 | 1/2001 | Schöllermann et al. |
| 6,184,521 B1 | 2/2001 | Coffin, IV et al. |
| 6,188,470 B1 | 2/2001 | Grace |
| 6,192,260 B1 | 2/2001 | Chance |
| 6,195,575 B1 | 2/2001 | Levinson |
| 6,198,951 B1 | 3/2001 | Kosuda et al. |
| 6,206,830 B1 | 3/2001 | Diab et al. |
| 6,213,952 B1 | 4/2001 | Finarov et al. |
| 6,217,523 B1 | 4/2001 | Amano et al. |
| 6,222,189 B1 | 4/2001 | Misner et al. |
| 6,223,064 B1 | 4/2001 | Lynn |
| 6,226,539 B1 | 5/2001 | Potratz |
| 6,226,540 B1 | 5/2001 | Bernreuter |
| 6,229,856 B1 | 5/2001 | Diab et al. |
| 6,230,035 B1 | 5/2001 | Aoyagi et al. |
| 6,233,470 B1 | 5/2001 | Tsuchiya |
| 6,236,871 B1 | 5/2001 | Tsuchiya |
| 6,236,872 B1 | 5/2001 | Diab et al. |
| 6,240,305 B1 | 5/2001 | Tsuchiya |
| 6,253,097 B1 | 6/2001 | Aronow et al. |
| 6,253,098 B1 | 6/2001 | Walker et al. |
| 6,256,523 B1 | 7/2001 | Diab et al. |
| 6,256,524 B1 | 7/2001 | Walker et al. |
| 6,261,236 B1 | 7/2001 | Grimblatov |
| 6,263,221 B1 | 7/2001 | Chance et al. |
| 6,263,222 B1 | 7/2001 | Diab et al. |
| 6,263,223 B1 | 7/2001 | Shepherd et al. |
| 6,266,546 B1 | 7/2001 | Steuer et al. |
| 6,266,547 B1 | 7/2001 | Walker et al. |
| 6,272,363 B1 | 8/2001 | Casciani et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,894 B1 | 9/2001 | Oppelt et al. |
| 6,285,895 B1 | 9/2001 | Ristolainen et al. |

| | | |
|---|---|---|
| 6,285,896 B1 | 9/2001 | Tobler et al. |
| 6,298,252 B1 | 10/2001 | Kovach et al. |
| 6,308,089 B1 | 10/2001 | Von der Ruhr et al. |
| 6,312,393 B1 | 11/2001 | Abreu |
| 6,321,100 B1 | 11/2001 | Parker |
| 6,330,468 B1 | 12/2001 | Scharf |
| 6,334,065 B1 | 12/2001 | Al-Ali et al. |
| 6,339,715 B1 | 1/2002 | Bahr et al. |
| 6,342,039 B1 | 1/2002 | Lynn |
| 6,343,223 B1 | 1/2002 | Chin et al. |
| 6,343,224 B1 | 1/2002 | Parker |
| 6,349,228 B1 | 2/2002 | Kiani et al. |
| 6,351,658 B1 | 2/2002 | Middleman et al. |
| 6,353,750 B1 | 3/2002 | Kimura et al. |
| 6,356,774 B1 | 3/2002 | Bernstein et al. |
| 6,360,113 B1 | 3/2002 | Dettling |
| 6,360,114 B1 | 3/2002 | Diab et al. |
| 6,361,501 B1 | 3/2002 | Amano et al. |
| 6,363,269 B1 | 3/2002 | Hanna et al. |
| D455,834 S | 4/2002 | Donars et al. |
| 6,370,408 B1 | 4/2002 | Merchant et al. |
| 6,370,409 B1 | 4/2002 | Chung et al. |
| 6,371,921 B1 | 4/2002 | Caro |
| 6,374,129 B1 | 4/2002 | Chin et al. |
| 6,377,829 B1 | 4/2002 | Al-Ali et al. |
| 6,381,479 B1 | 4/2002 | Norris |
| 6,381,480 B1 | 4/2002 | Stoddar et al. |
| 6,385,471 B1 | 5/2002 | Mortz |
| 6,385,821 B1 | 5/2002 | Modgil et al. |
| 6,388,240 B2 | 5/2002 | Schulz et al. |
| 6,393,310 B1 | 5/2002 | Kuenster |
| 6,393,311 B1 | 5/2002 | Edgar, Jr. et al. |
| 6,397,091 B2 | 5/2002 | Diab et al. |
| 6,397,092 B1 | 5/2002 | Norris et al. |
| 6,397,093 B1 | 5/2002 | Aldrich |
| 6,400,971 B1 | 6/2002 | Finarov et al. |
| 6,400,972 B1 | 6/2002 | Fine |
| 6,400,973 B1 | 6/2002 | Winter |
| 6,402,690 B1 | 6/2002 | Rhee et al. |
| 6,408,198 B1 | 6/2002 | Hanna et al. |
| 6,411,832 B1 | 6/2002 | Guthermann |
| 6,411,833 B1 | 6/2002 | Baker, Jr. et al. |
| 6,415,236 B2 | 7/2002 | Kobayashi et al. |
| 6,421,549 B1 | 7/2002 | Jacques |
| 6,430,423 B2 | 8/2002 | DeLonzor et al. |
| 6,430,513 B1 | 8/2002 | Wang et al. |
| 6,430,525 B1 | 8/2002 | Weber et al. |
| 6,434,408 B1 | 8/2002 | Heckel et al. |
| 6,438,396 B1 | 8/2002 | Cook |
| 6,438,399 B1 | 8/2002 | Kurth |
| 6,449,501 B1 | 9/2002 | Reuss |
| 6,453,183 B1 | 9/2002 | Walker |
| 6,453,184 B1 | 9/2002 | Hyogo et al. |
| 6,456,862 B2 | 9/2002 | Benni |
| 6,461,305 B1 | 10/2002 | Schnall |
| 6,463,310 B1 | 10/2002 | Swedlow et al. |
| 6,463,311 B1 | 10/2002 | Diab |
| 6,466,808 B1 | 10/2002 | Chin et al. |
| 6,466,809 B1 | 10/2002 | Riley |
| 6,470,199 B1 | 10/2002 | Kopotic et al. |
| 6,470,200 B2 | 10/2002 | Walker et al. |
| 6,480,729 B2 | 11/2002 | Stone |
| 6,487,439 B1 | 11/2002 | Skladnev et al. |
| 6,490,466 B1 | 12/2002 | Fein et al. |
| 6,493,568 B1 | 12/2002 | Bell |
| 6,496,711 B1 | 12/2002 | Athan et al. |
| 6,498,942 B1 | 12/2002 | Esenaliev et al. |
| 6,501,974 B2 | 12/2002 | Huiku |
| 6,501,975 B2 | 12/2002 | Diab et al. |
| 6,505,060 B1 | 1/2003 | Norris |
| 6,505,061 B2 | 1/2003 | Larson |
| 6,505,133 B1 | 1/2003 | Hanna et al. |
| 6,510,329 B2 | 1/2003 | Heckel |
| 6,510,331 B1 | 1/2003 | Williams et al. |
| 6,512,937 B2 | 1/2003 | Blank et al. |
| 6,515,273 B2 | 2/2003 | Al-Ali |
| 6,519,484 B1 | 2/2003 | Lovejoy et al. |
| 6,519,486 B1 | 2/2003 | Edgar, Jr. et al. |
| 6,519,487 B1 | 2/2003 | Parker |
| 6,525,386 B1 | 2/2003 | Mills et al. |
| 6,526,300 B1 | 2/2003 | Kiani et al. |
| 6,526,301 B2 | 2/2003 | Larsen et al. |
| 6,541,756 B2 | 4/2003 | Schulz et al. |
| 6,542,764 B1 | 4/2003 | Al-Ali et al. |
| 6,544,193 B2 | 4/2003 | Abreu |
| 6,546,267 B1 | 4/2003 | Sugiura et al. |
| 6,549,284 B1 | 4/2003 | Boas |
| 6,549,795 B1 | 4/2003 | Chance |
| 6,553,241 B2 | 4/2003 | Mannheimer et al. |
| 6,553,242 B1 | 4/2003 | Sarussi |
| 6,553,243 B2 | 4/2003 | Gurley |
| 6,554,788 B1 | 4/2003 | Hunley |
| 6,556,852 B1 | 4/2003 | Schulze et al. |
| 6,560,470 B1 | 5/2003 | Pologe |
| 6,564,077 B2 | 5/2003 | Mortara |
| 6,564,088 B1 | 5/2003 | Soller et al. |
| 6,571,113 B1 | 5/2003 | Fein et al. |
| 6,571,114 B1 | 5/2003 | Koike et al. |
| 6,574,491 B2 | 6/2003 | Elghazzawi |
| 6,580,086 B1 | 6/2003 | Schulz et al. |
| 6,584,336 B1 | 6/2003 | Ali et al. |
| 6,587,703 B2 | 7/2003 | Cheng et al. |
| 6,587,704 B1 | 7/2003 | Fine et al. |
| 6,589,172 B2 | 7/2003 | Williams et al. |
| 6,591,122 B2 | 7/2003 | Schmitt |
| 6,591,123 B2 | 7/2003 | Fein et al. |
| 6,594,511 B2 | 7/2003 | Stone et al. |
| 6,594,512 B2 | 7/2003 | Huang |
| 6,594,513 B1 | 7/2003 | Jobsis et al. |
| 6,597,931 B1 | 7/2003 | Cheng et al. |
| 6,597,933 B2 | 7/2003 | Kiani et al. |
| 6,600,940 B1 | 7/2003 | Fein et al. |
| 6,606,509 B2 | 8/2003 | Schmitt |
| 6,606,510 B2 | 8/2003 | Swedlow et al. |
| 6,606,511 B1 | 8/2003 | Ali et al. |
| 6,606,512 B2 | 8/2003 | Muz et al. |
| 6,608,562 B1 | 8/2003 | Kimura |
| 6,609,016 B1 | 8/2003 | Lynn |
| 6,615,064 B1 | 9/2003 | Aldrich |
| 6,615,065 B1 | 9/2003 | Barrett et al. |
| 6,618,602 B2 | 9/2003 | Levin |
| 6,622,034 B1 | 9/2003 | Gorski et al. |
| 6,622,095 B2 | 9/2003 | Kobayashi et al. |
| 6,628,975 B1 | 9/2003 | Fein et al. |
| 6,631,281 B1 | 10/2003 | Kästle |
| 6,632,181 B2 | 10/2003 | Flaherty |
| 6,640,116 B2 | 10/2003 | Diab |
| 6,643,530 B2 | 11/2003 | Diab et al. |
| 6,643,531 B1 | 11/2003 | Katarow |
| 6,647,279 B2 | 11/2003 | Pologe |
| 6,647,280 B2 | 11/2003 | Bahr et al. |
| 6,650,916 B2 | 11/2003 | Cook |
| 6,650,917 B2 | 11/2003 | Diab et al. |
| 6,650,918 B2 | 11/2003 | Terry |
| 6,654,621 B2 | 11/2003 | Palatnik et al. |
| 6,654,622 B1 | 11/2003 | Eberhard et al. |
| 6,654,623 B1 | 11/2003 | Kästle |
| 6,654,624 B2 | 11/2003 | Diab et al. |
| 6,658,276 B2 | 12/2003 | Kianl et al. |
| 6,658,277 B2 | 12/2003 | Wasserman |
| 6,662,030 B2 | 12/2003 | Khalil et al. |
| 6,662,033 B2 | 12/2003 | Casciani et al. |
| 6,665,551 B1 | 12/2003 | Suzuki |
| 6,668,182 B2 | 12/2003 | Hubelbank |
| 6,668,183 B2 | 12/2003 | Hicks et al. |
| 6,671,526 B1 | 12/2003 | Aoyagi et al. |
| 6,671,528 B2 | 12/2003 | Steuer et al. |
| 6,671,530 B2 | 12/2003 | Chung et al. |
| 6,671,531 B2 | 12/2003 | Al-Ali et al. |
| 6,671,532 B1 | 12/2003 | Fudge et al. |
| 6,675,031 B1 | 1/2004 | Porges et al. |
| 6,678,543 B2 | 1/2004 | Diab et al. |
| 6,681,126 B2 | 1/2004 | Solenberger |
| 6,681,128 B2 | 1/2004 | Steuer et al. |
| 6,681,454 B2 | 1/2004 | Modgil et al. |
| 6,684,090 B2 | 1/2004 | Ali et al. |
| 6,684,091 B2 | 1/2004 | Parker |
| 6,687,519 B2 | 2/2004 | Steuer et al. |

| Patent | Kind | Date | Inventor |
|---|---|---|---|
| 6,690,958 | B1 | 2/2004 | Walker et al. |
| 6,694,160 | B2 | 2/2004 | Chin |
| 6,697,653 | B2 | 2/2004 | Hanna |
| 6,697,655 | B2 | 2/2004 | Sueppel et al. |
| 6,697,656 | B1 | 2/2004 | Al-Ali |
| 6,697,658 | B2 | 2/2004 | Al-Ali |
| RE38,476 | E | 3/2004 | Diab et al. |
| 6,699,194 | B1 | 3/2004 | Diab et al. |
| 6,699,199 | B2 | 3/2004 | Asada et al. |
| 6,701,170 | B2 | 3/2004 | Stetson |
| 6,702,752 | B2 | 3/2004 | Dekker |
| 6,707,257 | B2 | 3/2004 | Norris |
| 6,708,048 | B1 | 3/2004 | Chance |
| 6,708,049 | B1 | 3/2004 | Berson et al. |
| 6,709,402 | B2 | 3/2004 | Dekker |
| 6,711,424 | B1 | 3/2004 | Fine et al. |
| 6,711,425 | B1 | 3/2004 | Reuss |
| 6,712,762 | B1 | 3/2004 | Lichter |
| 6,714,803 | B1 | 3/2004 | Mortz |
| 6,714,804 | B2 | 3/2004 | Al-Ali et al. |
| 6,714,805 | B2 | 3/2004 | Jeon et al. |
| RE38,492 | E | 4/2004 | Diab et al. |
| 6,719,686 | B2 | 4/2004 | Coakley et al. |
| 6,719,705 | B2 | 4/2004 | Mills |
| 6,720,734 | B2 | 4/2004 | Norris |
| 6,721,584 | B2 | 4/2004 | Baker, Jr. et al. |
| 6,721,585 | B1 | 4/2004 | Parker |
| 6,725,074 | B1 | 4/2004 | Kästle |
| 6,725,075 | B2 | 4/2004 | Al-Ali |
| 6,731,962 | B1 | 5/2004 | Katarow |
| 6,731,963 | B2 | 5/2004 | Finarov et al. |
| 6,731,967 | B1 | 5/2004 | Turcott |
| 6,735,459 | B2 | 5/2004 | Parker |
| 6,745,060 | B2 | 6/2004 | Diab et al. |
| 6,745,061 | B1 | 6/2004 | Hicks et al. |
| 6,748,253 | B2 | 6/2004 | Norris et al. |
| 6,748,254 | B2 | 6/2004 | O'Neil et al. |
| 6,754,515 | B1 | 6/2004 | Pologe |
| 6,754,516 | B2 | 6/2004 | Mannheimer |
| 6,760,607 | B2 | 7/2004 | Al-All |
| 6,760,609 | B2 | 7/2004 | Jacques |
| 6,760,610 | B2 | 7/2004 | Tscupp et al. |
| 6,763,255 | B2 | 7/2004 | DeLonzor et al. |
| 6,763,256 | B2 | 7/2004 | Kimball et al. |
| 6,770,028 | B1 | 8/2004 | Ali et al. |
| 6,771,994 | B2 | 8/2004 | Kiani et al. |
| 6,773,397 | B2 | 8/2004 | Kelly |
| 6,778,923 | B2 | 8/2004 | Norris et al. |
| 6,780,158 | B2 | 8/2004 | Yarita |
| 6,785,568 | B2 | 8/2004 | Chance |
| 6,791,689 | B1 | 9/2004 | Weckstrom |
| 6,792,300 | B1 | 9/2004 | Diab et al. |
| 6,801,797 | B2 | 10/2004 | Mannheimer et al. |
| 6,801,798 | B2 | 10/2004 | Geddes et al. |
| 6,801,799 | B2 | 10/2004 | Mendelson |
| 6,801,802 | B2 | 10/2004 | Sitzman et al. |
| 6,802,812 | B1 | 10/2004 | Walker et al. |
| 6,805,673 | B2 | 10/2004 | Dekker |
| 6,810,277 | B2 | 10/2004 | Edgar, Jr. et al. |
| 6,813,511 | B2 | 11/2004 | Diab et al. |
| 6,816,741 | B2 | 11/2004 | Diab |
| 6,819,950 | B2 | 11/2004 | Mills |
| 6,822,564 | B2 | 11/2004 | Al-Ali |
| 6,825,619 | B2 | 11/2004 | Norris |
| 6,826,419 | B2 | 11/2004 | Diab et al. |
| 6,829,496 | B2 | 12/2004 | Nagai et al. |
| 6,830,711 | B2 | 12/2004 | Mills et al. |
| 6,836,679 | B2 | 12/2004 | Baker, Jr. et al. |
| 6,839,579 | B1 | 1/2005 | Chin |
| 6,839,580 | B2 | 1/2005 | Zonios et al. |
| 6,839,582 | B2 | 1/2005 | Heckel |
| 6,839,659 | B2 | 1/2005 | Tarassenko et al. |
| 6,842,635 | B1 | 1/2005 | Parker |
| 6,845,256 | B2 | 1/2005 | Chin et al. |
| 6,850,787 | B2 | 2/2005 | Weber et al. |
| 6,850,788 | B2 | 2/2005 | Al-Ali |
| 6,850,789 | B2 | 2/2005 | Schweitzer, Jr. et al. |
| 6,852,083 | B2 | 2/2005 | Caro |
| 6,861,639 | B2 | 3/2005 | Al-Ali |
| 6,863,652 | B2 | 3/2005 | Huang et al. |
| 6,865,407 | B2 | 3/2005 | Kimball et al. |
| 6,873,865 | B2 | 3/2005 | Steuer et al. |
| 6,879,850 | B2 | 4/2005 | Kimball |
| 6,882,874 | B2 | 4/2005 | Huiku |
| 6,889,153 | B2 | 5/2005 | Dietiker |
| 6,898,452 | B2 | 5/2005 | Al-Ali et al. |
| 6,909,912 | B2 | 6/2005 | Melker et al. |
| 6,912,413 | B2 | 6/2005 | Rantala et al. |
| 6,916,289 | B2 | 7/2005 | Schnall |
| 6,920,345 | B2 | 7/2005 | Al-Ali et al. |
| 6,931,269 | B2 | 8/2005 | Terry |
| 6,934,570 | B2 | 8/2005 | Kiani et al. |
| 6,941,162 | B2 | 9/2005 | Fudge et al. |
| 6,947,781 | B2 | 9/2005 | Asada et al. |
| 6,949,081 | B1 | 9/2005 | Chance |
| 6,950,687 | B2 | 9/2005 | Al-Ali |
| 6,954,664 | B2 | 10/2005 | Sweitzer |
| 6,961,598 | B2 | 11/2005 | Diab |
| 6,963,767 | B2 | 11/2005 | Rantala et al. |
| 6,968,221 | B2 | 11/2005 | Rosenthal |
| 6,971,580 | B2 | 12/2005 | Zhu et al. |
| 6,979,812 | B2 | 12/2005 | Al-Ali |
| 6,983,178 | B2 | 1/2006 | Fine et al. |
| 6,985,763 | B2 | 1/2006 | Boas et al. |
| 6,985,764 | B2 | 1/2006 | Mason et al. |
| 6,990,426 | B2 | 1/2006 | Yoon et al. |
| 6,992,751 | B2 | 1/2006 | Okita et al. |
| 6,992,772 | B2 | 1/2006 | Block |
| 6,993,371 | B2 | 1/2006 | Kiani et al. |
| 6,993,372 | B2 | 1/2006 | Fine et al. |
| 6,996,427 | B2 | 2/2006 | Ali et al. |
| 6,997,880 | B2 | 2/2006 | Carlebach |
| 6,999,904 | B2 | 2/2006 | Weber |
| 7,003,338 | B2 | 2/2006 | Weber et al. |
| 7,003,339 | B2 | 2/2006 | Diab et al. |
| 7,006,855 | B1 | 2/2006 | Sarussi |
| 7,006,856 | B2 | 2/2006 | Baker, Jr. et al. |
| 7,016,715 | B2 | 3/2006 | Stetson |
| 7,020,507 | B2 | 3/2006 | Scharf et al. |
| 7,024,233 | B2 | 4/2006 | Ali et al. |
| 7,024,235 | B2 | 4/2006 | Melker et al. |
| 7,025,728 | B2 | 4/2006 | Ito et al. |
| 7,027,849 | B2 | 4/2006 | Al-Ali |
| 7,027,850 | B2 | 4/2006 | Wasserman |
| 7,039,449 | B2 | 5/2006 | Al-Ali |
| 7,039,538 | B2 | 5/2006 | Baker, Jr. |
| 7,043,289 | B2 | 5/2006 | Fine et al. |
| 7,047,055 | B2 | 5/2006 | Boas et al. |
| 7,060,035 | B2 | 6/2006 | Wasserman |
| 7,062,307 | B2 | 6/2006 | Norris et al. |
| 7,067,893 | B2 | 6/2006 | Mills et al. |
| 7,072,701 | B2 | 7/2006 | Chen et al. |
| 7,072,702 | B2 | 7/2006 | Edgar, Jr. et al. |
| 7,079,880 | B2 | 7/2006 | Stetson |
| 7,085,597 | B2 | 8/2006 | Fein et al. |
| 7,096,052 | B2 | 8/2006 | Mason et al. |
| 7,096,054 | B2 | 8/2006 | Abdul-Hafiz et al. |
| 7,107,088 | B2 | 9/2006 | Aceti |
| 7,113,815 | B2 | 9/2006 | O'Neil et al. |
| 7,120,480 | B2 | 10/2006 | Chew |
| 7,123,950 | B2 | 10/2006 | Mannheimer |
| 7,124,048 | B2 | 10/2006 | Dietiker |
| 7,127,278 | B2 | 10/2006 | Melker et al. |
| 7,130,671 | B2 | 10/2006 | Baker, Jr. et al. |
| 7,132,641 | B2 | 11/2006 | Schulz et al. |
| 7,133,711 | B2 | 11/2006 | Chernoguz et al. |
| 7,139,599 | B2 | 11/2006 | Terry |
| 7,142,901 | B2 | 11/2006 | Kiani et al. |
| 7,162,288 | B2 | 1/2007 | Nordstrom |
| 7,190,987 | B2 | 3/2007 | Lindekugel et al. |
| 7,198,778 | B2 | 4/2007 | Achilefu et al. |
| 7,209,774 | B2 | 4/2007 | Baker, Jr. |
| 7,215,984 | B2 | 5/2007 | Diab et al. |
| 7,215,985 | B2 | 5/2007 | Petersen |
| 7,225,006 | B2 | 5/2007 | Al-Ali et al. |
| 7,228,161 | B2 | 6/2007 | Chin |
| 7,236,811 | B2 | 6/2007 | Schmitt et al. |
| 7,239,901 | B2 | 7/2007 | Gritsenko |

| Patent/Pub. No. | Kind | Date | Inventor(s) |
|---|---|---|---|
| 7,248,910 | B2 | 7/2007 | Li et al. |
| 7,254,433 | B2 | 8/2007 | Diab et al. |
| 7,254,434 | B2 | 8/2007 | Schulz et al. |
| 7,272,425 | B2 | 9/2007 | Al-Ali |
| 7,274,955 | B2 | 9/2007 | Kiani |
| 7,277,741 | B2 | 10/2007 | Debreczeny et al. |
| 7,280,858 | B2 | 10/2007 | Al-Ali et al. |
| 7,295,866 | B2 | 11/2007 | Al-Ali |
| 7,305,262 | B2 | 12/2007 | Brodnick et al. |
| 7,315,753 | B2 | 1/2008 | Baker, Jr. et al. |
| 7,349,726 | B2 | 3/2008 | Casciani |
| 7,350,919 | B2 | 4/2008 | Hillis |
| 7,373,192 | B2 | 5/2008 | Chew |
| 7,376,454 | B2 | 5/2008 | Casciani |
| 7,428,432 | B2 | 9/2008 | Al-Ali |
| 7,438,683 | B2 | 10/2008 | Al-Ali |
| 7,460,909 | B1 | 12/2008 | Koh |
| 8,000,760 | B2 * | 8/2011 | Mannheimer et al. ........ 600/323 |
| 2001/0005773 | A1 | 6/2001 | Larsen et al. |
| 2001/0020122 | A1 | 9/2001 | Steuer et al. |
| 2001/0021803 | A1 | 9/2001 | Blank et al. |
| 2001/0039376 | A1 | 11/2001 | Steuer et al. |
| 2001/0044700 | A1 | 11/2001 | Kobayashi et al. |
| 2001/0051767 | A1 | 12/2001 | Williams et al. |
| 2002/0016537 | A1 | 2/2002 | Muz et al. |
| 2002/0026106 | A1 | 2/2002 | Khalil et al. |
| 2002/0026109 | A1 | 2/2002 | Diab et al. |
| 2002/0028990 | A1 | 3/2002 | Shepherd et al. |
| 2002/0035318 | A1 | 3/2002 | Mannheimer et al. |
| 2002/0038078 | A1 | 3/2002 | Ito |
| 2002/0038079 | A1 | 3/2002 | Steuer et al. |
| 2002/0042558 | A1 | 4/2002 | Mendelson |
| 2002/0049389 | A1 | 4/2002 | Abreu |
| 2002/0062071 | A1 | 5/2002 | Diab et al. |
| 2002/0068859 | A1 | 6/2002 | Knopp |
| 2002/0072681 | A1 | 6/2002 | Schnall |
| 2002/0082489 | A1 | 6/2002 | Casciani |
| 2002/0103423 | A1 | 8/2002 | Chin |
| 2002/0111748 | A1 | 8/2002 | Kobayashi et al. |
| 2002/0116797 | A1 | 8/2002 | Modgil et al. |
| 2002/0128544 | A1 | 9/2002 | Diab et al. |
| 2002/0133067 | A1 | 9/2002 | Jackson, III |
| 2002/0133068 | A1 | 9/2002 | Huiku |
| 2002/0156354 | A1 | 10/2002 | Larson |
| 2002/0161287 | A1 | 10/2002 | Schmitt |
| 2002/0161290 | A1 | 10/2002 | Chance |
| 2002/0165439 | A1 | 11/2002 | Schmitt |
| 2002/0173706 | A1 | 11/2002 | Takatani |
| 2002/0173709 | A1 | 11/2002 | Fine et al. |
| 2002/0190863 | A1 | 12/2002 | Lynn |
| 2002/0198442 | A1 | 12/2002 | Rantala et al. |
| 2002/0198443 | A1 | 12/2002 | Ting |
| 2003/0018243 | A1 | 1/2003 | Gerhardt et al. |
| 2003/0023140 | A1 | 1/2003 | Chance |
| 2003/0036690 | A1 | 2/2003 | Geddes et al. |
| 2003/0045785 | A1 | 3/2003 | Diab et al. |
| 2003/0055324 | A1 | 3/2003 | Wasserman |
| 2003/0060693 | A1 | 3/2003 | Monfre et al. |
| 2003/0073889 | A1 | 4/2003 | Keilbach et al. |
| 2003/0073890 | A1 | 4/2003 | Hanna |
| 2003/0100840 | A1 | 5/2003 | Sugiura et al. |
| 2003/0132495 | A1 | 7/2003 | Mills et al. |
| 2003/0135099 | A1 | 7/2003 | Al-Ali |
| 2003/0139687 | A1 | 7/2003 | Abreu |
| 2003/0144584 | A1 | 7/2003 | Mendelson |
| 2003/0162414 | A1 | 8/2003 | Schulz et al. |
| 2003/0171662 | A1 | 9/2003 | O'Connor et al. |
| 2003/0176776 | A1 | 9/2003 | Huiku |
| 2003/0181799 | A1 | 9/2003 | Lindekugel et al. |
| 2003/0187337 | A1 | 10/2003 | Tarassenko et al. |
| 2003/0195402 | A1 | 10/2003 | Fein et al. |
| 2003/0197679 | A1 | 10/2003 | Ali et al. |
| 2003/0212316 | A1 | 11/2003 | Leiden et al. |
| 2003/0220548 | A1 | 11/2003 | Schmitt |
| 2003/0220576 | A1 | 11/2003 | Diab |
| 2003/0225323 | A1 | 12/2003 | Kiani et al. |
| 2003/0225337 | A1 | 12/2003 | Scharf et al. |
| 2003/0236452 | A1 | 12/2003 | Melker et al. |
| 2003/0236647 | A1 | 12/2003 | Yoon et al. |
| 2004/0006261 | A1 | 1/2004 | Swedlow et al. |
| 2004/0010188 | A1 | 1/2004 | Wasserman |
| 2004/0024297 | A1 | 2/2004 | Chen et al. |
| 2004/0024326 | A1 | 2/2004 | Yeo et al. |
| 2004/0034293 | A1 | 2/2004 | Kimball |
| 2004/0039272 | A1 | 2/2004 | Abdul-Hafiz et al. |
| 2004/0039273 | A1 | 2/2004 | Terry |
| 2004/0054269 | A1 | 3/2004 | Rantala et al. |
| 2004/0054270 | A1 | 3/2004 | Pewzner et al. |
| 2004/0054291 | A1 | 3/2004 | Schulz et al. |
| 2004/0059209 | A1 | 3/2004 | Al-Ali et al. |
| 2004/0059210 | A1 | 3/2004 | Stetson |
| 2004/0064020 | A1 | 4/2004 | Diab et al. |
| 2004/0068164 | A1 | 4/2004 | Diab et al. |
| 2004/0087846 | A1 | 5/2004 | Wasserman |
| 2004/0092805 | A1 | 5/2004 | Yarita |
| 2004/0097797 | A1 | 5/2004 | Porges et al. |
| 2004/0098009 | A1 | 5/2004 | Boecker et al. |
| 2004/0107065 | A1 | 6/2004 | Al-Ali |
| 2004/0116788 | A1 | 6/2004 | Chernoguz et al. |
| 2004/0116789 | A1 | 6/2004 | Boas et al. |
| 2004/0117891 | A1 | 6/2004 | Hannula et al. |
| 2004/0122300 | A1 | 6/2004 | Boas et al. |
| 2004/0122302 | A1 | 6/2004 | Mason et al. |
| 2004/0127779 | A1 | 7/2004 | Steuer et al. |
| 2004/0133087 | A1 | 7/2004 | Ali et al. |
| 2004/0133088 | A1 | 7/2004 | Al-Ali et al. |
| 2004/0138538 | A1 | 7/2004 | Stetson |
| 2004/0138540 | A1 | 7/2004 | Baker, Jr. et al. |
| 2004/0143172 | A1 | 7/2004 | Fudge et al. |
| 2004/0147821 | A1 | 7/2004 | Al-Ali et al. |
| 2004/0147822 | A1 | 7/2004 | Al-Ali et al. |
| 2004/0147823 | A1 | 7/2004 | Kiani et al. |
| 2004/0147824 | A1 | 7/2004 | Diab et al. |
| 2004/0152965 | A1 | 8/2004 | Diab et al. |
| 2004/0158134 | A1 | 8/2004 | Diab et al. |
| 2004/0158135 | A1 | 8/2004 | Baker, Jr. et al. |
| 2004/0162472 | A1 | 8/2004 | Berson et al. |
| 2004/0167381 | A1 | 8/2004 | Lichter |
| 2004/0171920 | A1 | 9/2004 | Mannheimer et al. |
| 2004/0171948 | A1 | 9/2004 | Terry |
| 2004/0176670 | A1 | 9/2004 | Takamura et al. |
| 2004/0176671 | A1 | 9/2004 | Fine et al. |
| 2004/0181133 | A1 | 9/2004 | Al-Ali et al. |
| 2004/0181134 | A1 | 9/2004 | Baker, Jr. et al. |
| 2004/0186358 | A1 | 9/2004 | Chernow et al. |
| 2004/0199063 | A1 | 10/2004 | O'Neil et al. |
| 2004/0204636 | A1 | 10/2004 | Diab et al. |
| 2004/0204637 | A1 | 10/2004 | Diab et al. |
| 2004/0204638 | A1 | 10/2004 | Diab et al. |
| 2004/0204639 | A1 | 10/2004 | Casciani et al. |
| 2004/0204865 | A1 | 10/2004 | Lee et al. |
| 2004/0210146 | A1 | 10/2004 | Diab et al. |
| 2004/0215069 | A1 | 10/2004 | Mannheimer |
| 2004/0215085 | A1 | 10/2004 | Schnall |
| 2004/0230106 | A1 | 11/2004 | Schmitt et al. |
| 2004/0230107 | A1 | 11/2004 | Asada et al. |
| 2004/0230108 | A1 | 11/2004 | Melker et al. |
| 2004/0236196 | A1 | 11/2004 | Diab et al. |
| 2004/0242980 | A1 | 12/2004 | Kiani et al. |
| 2004/0249252 | A1 | 12/2004 | Fine et al. |
| 2004/0257557 | A1 | 12/2004 | Block et al. |
| 2004/0260161 | A1 | 12/2004 | Melker et al. |
| 2004/0267103 | A1 | 12/2004 | Li et al. |
| 2004/0267104 | A1 | 12/2004 | Hannula et al. |
| 2004/0267140 | A1 | 12/2004 | Ito et al. |
| 2005/0004479 | A1 | 1/2005 | Townsend et al. |
| 2005/0010092 | A1 | 1/2005 | Weber et al. |
| 2005/0014999 | A1 | 1/2005 | Rahe-Meyer |
| 2005/0020887 | A1 | 1/2005 | Goldberg |
| 2005/0020894 | A1 | 1/2005 | Norris et al. |
| 2005/0033128 | A1 | 2/2005 | Ali et al. |
| 2005/0033129 | A1 | 2/2005 | Edgar, Jr. et al. |
| 2005/0033131 | A1 | 2/2005 | Chen |
| 2005/0043599 | A1 | 2/2005 | O'Mara |
| 2005/0043600 | A1 | 2/2005 | Diab et al. |
| 2005/0049468 | A1 | 3/2005 | Carlson |
| 2005/0049470 | A1 | 3/2005 | Terry |
| 2005/0049471 | A1 | 3/2005 | Aceti |

| | | | | | | |
|---|---|---|---|---|---|---|
| 2005/0065417 A1 | 3/2005 | Al-Ali | | 2007/0073127 A1 | 3/2007 | Kiani |
| 2005/0070773 A1 | 3/2005 | Chin | | 2007/0088207 A1 | 4/2007 | Mannheimer |
| 2005/0075546 A1 | 4/2005 | Samsoondar | | 2007/0100220 A1 | 5/2007 | Baker, Jr. |
| 2005/0075550 A1 | 4/2005 | Lindekugel | | 2007/0112260 A1 | 5/2007 | Diab |
| 2005/0080323 A1 | 4/2005 | Kato | | 2007/0208236 A1 | 9/2007 | Hicks |
| 2005/0085704 A1 | 4/2005 | Schulz | | 2007/0225614 A1 | 9/2007 | Naghavi |
| 2005/0090720 A1 | 4/2005 | Wu | | 2007/0244376 A1 | 10/2007 | Wang |
| 2005/0101850 A1 | 5/2005 | Parker | | 2008/0015424 A1 | 1/2008 | Bernreuter |
| 2005/0107676 A1 | 5/2005 | Acosta et al. | | 2008/0039701 A1 | 2/2008 | Al-Ali |
| 2005/0113656 A1 | 5/2005 | Chance | | 2008/0221427 A1 | 9/2008 | Petersen |
| 2005/0168722 A1 | 8/2005 | Forstner et al. | | | | |
| 2005/0192488 A1 | 9/2005 | Bryenton et al. | | FOREIGN PATENT DOCUMENTS | | |
| 2005/0197548 A1 | 9/2005 | Dietiker | | DE | 3405444 | 8/1985 |
| 2005/0197551 A1 | 9/2005 | Al-Ali | | DE | 3516338 | 11/1986 |
| 2005/0203357 A1 | 9/2005 | Debreczeny et al. | | DE | 37 03 458 | 8/1988 |
| 2005/0222502 A1 | 10/2005 | Cooper | | DE | 3938759 | 5/1991 |
| 2005/0228248 A1 | 10/2005 | Dietiker | | DE | 4210102 A1 | 9/1993 |
| 2005/0250998 A1 | 11/2005 | Huiku | | DE | 4423597 | 8/1995 |
| 2005/0256386 A1 | 11/2005 | Chan | | DE | 19632361 | 2/1997 |
| 2005/0267346 A1 | 12/2005 | Faber et al. | | DE | 69123448 | 5/1997 |
| 2005/0272986 A1 | 12/2005 | Smith | | DE | 19703220 | 7/1997 |
| 2005/0277819 A1 | 12/2005 | Kiani et al. | | DE | 19640807 A1 | 9/1997 |
| 2006/0009688 A1 | 1/2006 | Lamego et al. | | DE | 19647877 A1 | 4/1998 |
| 2006/0015021 A1 | 1/2006 | Cheng | | DE | 10030862 | 1/2002 |
| 2006/0020179 A1 | 1/2006 | Anderson | | DE | 102 13 692 A1 | 10/2003 |
| 2006/0020181 A1 | 1/2006 | Schmitt | | DE | 20318882 U1 | 4/2004 |
| 2006/0020185 A1 | 1/2006 | Al-Ali | | EP | 0127947 | 5/1984 |
| 2006/0030763 A1 | 2/2006 | Mannheimer et al. | | EP | 00194105 B1 | 9/1986 |
| 2006/0030764 A1 | 2/2006 | Porges | | EP | 00204459 A3 | 12/1986 |
| 2006/0052680 A1 | 3/2006 | Diab | | EP | 0 262 779 | 4/1988 |
| 2006/0058594 A1 | 3/2006 | Ishizuka et al. | | EP | 0315040 | 10/1988 |
| 2006/0058683 A1 | 3/2006 | Chance | | EP | 0314331 | 5/1989 |
| 2006/0074280 A1 | 4/2006 | Martis | | EP | 00352923 A1 | 1/1990 |
| 2006/0084852 A1 | 4/2006 | Mason et al. | | EP | 0 360 977 | 4/1990 |
| 2006/0084878 A1 | 4/2006 | Banet | | EP | 00430340 A3 | 6/1991 |
| 2006/0089547 A1 | 4/2006 | Sarussi | | EP | 0435 500 | 7/1991 |
| 2006/0106294 A1 | 5/2006 | Maser et al. | | EP | 0572684 | 5/1992 |
| 2006/0122517 A1 | 6/2006 | Banet | | EP | 00497021 A1 | 8/1992 |
| 2006/0129039 A1 | 6/2006 | Lindner | | EP | 0529412 | 8/1992 |
| 2006/0155198 A1 | 7/2006 | Schmid | | EP | 0531631 | 9/1992 |
| 2006/0173257 A1 | 8/2006 | Nagai | | EP | 0566354 | 4/1993 |
| 2006/0195026 A1 | 8/2006 | Casciani | | EP | 0587009 | 8/1993 |
| 2006/0195027 A1 | 8/2006 | Casciani | | EP | 00630203 B1 | 9/1993 |
| 2006/0200018 A1 | 9/2006 | Al-Ali | | EP | 0 572 684 | 12/1993 |
| 2006/0211925 A1 | 9/2006 | Lamego | | EP | 00615723 A1 | 9/1994 |
| 2006/0211929 A1 | 9/2006 | Casciani | | EP | 00702931 a1 | 3/1996 |
| 2006/0217604 A1 | 9/2006 | Fein | | EP | 00724860 A1 | 8/1996 |
| 2006/0217605 A1 | 9/2006 | Fein | | EP | 00793942 A3 | 9/1997 |
| 2006/0217606 A1 | 9/2006 | Fein | | EP | 0 864 293 | 9/1998 |
| 2006/0217607 A1 | 9/2006 | Fein | | EP | 01006863 B1 | 10/1998 |
| 2006/0217608 A1 | 9/2006 | Fein | | EP | 01006864 B1 | 10/1998 |
| 2006/0224059 A1 | 10/2006 | Swedlow | | EP | 0875199 | 11/1998 |
| 2006/0229510 A1 | 10/2006 | Fein | | EP | 00998214 A1 | 12/1998 |
| 2006/0229511 A1 | 10/2006 | Fein | | EP | 0 898 933 | 3/1999 |
| 2006/0253007 A1 | 11/2006 | Cheng | | EP | 0898933 | 3/1999 |
| 2006/0258923 A1 | 11/2006 | Al-Ali | | EP | 01332713 A1 | 8/2003 |
| 2006/0258924 A1 | 11/2006 | Al-Ali | | EP | 01469773 A1 | 8/2003 |
| 2006/0258925 A1 | 11/2006 | Al-Ali | | EP | 1502529 | 7/2004 |
| 2006/0258926 A1 | 11/2006 | Al-Ali | | EP | 01491135 A2 | 12/2004 |
| 2006/0270920 A1 | 11/2006 | Al-Ali | | EP | 1828731 | 9/2007 |
| 2006/0281983 A1 | 12/2006 | Al-Ali | | FR | 2685865 | 1/1992 |
| 2007/0032710 A1 | 2/2007 | Raridan et al. | | GB | 2 259 545 | 3/1993 |
| 2007/0032712 A1 | 2/2007 | Raridan et al. | | JP | 63275325 A | 11/1988 |
| 2007/0032715 A1 | 2/2007 | Eghbal et al. | | JP | 2013450 A | 1/1990 |
| 2007/0043269 A1 | 2/2007 | Mannheimer | | JP | 2111343 A | 4/1990 |
| 2007/0043270 A1 | 2/2007 | Mannheimer | | JP | 02 191434 | 7/1990 |
| 2007/0043271 A1 | 2/2007 | Mannheimer | | JP | 2237544 A | 9/1990 |
| 2007/0043272 A1 | 2/2007 | Mannheimer | | JP | 03 173536 | 7/1991 |
| 2007/0043273 A1 | 2/2007 | Mannheimer | | JP | 3170866 A | 7/1991 |
| 2007/0043274 A1 | 2/2007 | Mannheimer | | JP | 3245042 A | 10/1991 |
| 2007/0043275 A1 | 2/2007 | Mannheimer | | JP | 4174648 A | 6/1992 |
| 2007/0043276 A1 | 2/2007 | Mannheimer | | JP | 4191642 A | 7/1992 |
| 2007/0043277 A1 | 2/2007 | Mannheimer | | JP | 4332536 A | 11/1992 |
| 2007/0043278 A1 | 2/2007 | Mannheimer | | JP | 3124073 B | 3/1993 |
| 2007/0043279 A1 | 2/2007 | Mannheimer | | JP | 5049624 A | 3/1993 |
| 2007/0043280 A1 | 2/2007 | Mannheimer | | JP | 5049625 A | 3/1993 |
| 2007/0043282 A1 | 2/2007 | Mannheimer | | JP | 3115374 B | 4/1993 |
| 2007/0049810 A1 | 3/2007 | Mannheimer | | JP | 05 200031 | 8/1993 |
| 2007/0073126 A1 | 3/2007 | Raridan, Jr. | | JP | 5-212016 | 8/1993 |

| | | |
|---|---|---|
| JP | 2005/200031 | 8/1993 |
| JP | 5212016 A | 8/1993 |
| JP | 06 014906 | 1/1994 |
| JP | 06014906 | 1/1994 |
| JP | 6016774 B2 | 3/1994 |
| JP | 3116255 B | 4/1994 |
| JP | 6029504 U | 4/1994 |
| JP | 6098881 A | 4/1994 |
| JP | 06 154177 | 6/1994 |
| JP | 6269430 A | 9/1994 |
| JP | 6285048 A | 10/1994 |
| JP | 7001273 B2 | 1/1995 |
| JP | 7124138 A | 5/1995 |
| JP | 7136150 A | 5/1995 |
| JP | 3116259 B | 6/1995 |
| JP | 3116260 B | 6/1995 |
| JP | 7155311 A | 6/1995 |
| JP | 7155313 A | 6/1995 |
| JP | 3238813 B2 | 7/1995 |
| JP | 7171139 A | 7/1995 |
| JP | 3134144 B | 9/1995 |
| JP | 7236625 A | 9/1995 |
| JP | 7246191 A | 9/1995 |
| JP | 8256996 A | 10/1996 |
| JP | 9192120 A | 7/1997 |
| JP | 10216113 A | 8/1998 |
| JP | 10216114 A | 8/1998 |
| JP | 10216115 A | 8/1998 |
| JP | 10337282 A | 12/1998 |
| JP | 11019074 A | 1/1999 |
| JP | 11155841 A | 6/1999 |
| JP | 11 188019 | 7/1999 |
| JP | 11244268 A | 9/1999 |
| JP | 20107157 A | 4/2000 |
| JP | 20237170 A | 9/2000 |
| JP | 21245871 A | 9/2001 |
| JP | 22224088 A | 8/2002 |
| JP | 22282242 A | 10/2002 |
| JP | 23153881 A | 5/2003 |
| JP | 23153882 A | 5/2003 |
| JP | 23169791 A | 6/2003 |
| JP | 23194714 A | 7/2003 |
| JP | 23210438 A | 7/2003 |
| JP | 23275192 A | 9/2003 |
| JP | 23339678 A | 12/2003 |
| JP | 24008572 A | 1/2004 |
| JP | 24089546 A | 3/2004 |
| JP | 24113353 | 4/2004 |
| JP | 24113353 A | 4/2004 |
| JP | 24135854 A | 5/2004 |
| JP | 24148069 A | 5/2004 |
| JP | 24148070 A | 5/2004 |
| JP | 24159810 A | 6/2004 |
| JP | 24166775 A | 6/2004 |
| JP | 24194908 A | 7/2004 |
| JP | 24202190 A | 7/2004 |
| JP | 24248819 A | 9/2004 |
| JP | 24248820 A | 9/2004 |
| JP | 24261364 A | 9/2004 |
| JP | 24290412 A | 10/2004 |
| JP | 24290544 A | 10/2004 |
| JP | 24290545 A | 10/2004 |
| JP | 24329406 A | 11/2004 |
| JP | 24329607 A | 11/2004 |
| JP | 24329928 A | 11/2004 |
| JP | 24337605 A | 12/2004 |
| JP | 24344367 A | 12/2004 |
| JP | 24351107 A | 12/2004 |
| JP | 25034472 A | 2/2005 |
| JP | 27330708 A2 | 12/2007 |
| WO | WO 98/09566 A1 | 10/1989 |
| WO | WO 90/001293 A1 | 2/1990 |
| WO | WO 90/04352 | 5/1990 |
| WO | WO 91/01678 A1 | 2/1991 |
| WO | WO 91/11137 A1 | 8/1991 |
| WO | WO 92/00513 | 1/1992 |
| WO | WO 92/20273 | 11/1992 |
| WO | WO 92/21281 | 12/1992 |
| WO | WO 92/21281 A1 | 12/1992 |
| WO | WO 93/09711 | 5/1993 |
| WO | WO 93/13706 A2 | 7/1993 |
| WO | WO 93/16629 A1 | 9/1993 |
| WO | WO 94/03102 | 2/1994 |
| WO | WO 94/03102 A1 | 2/1994 |
| WO | WO 94/23643 | 10/1994 |
| WO | WO 94/23643 A1 | 10/1994 |
| WO | WO 95/02358 | 1/1995 |
| WO | WO 95/12349 A1 | 5/1995 |
| WO | WO 95/16970 | 6/1995 |
| WO | WO9526676 | 10/1995 |
| WO | WO 96/13208 | 5/1996 |
| WO | WO 96/39927 A1 | 12/1996 |
| WO | WO 97/36536 | 10/1997 |
| WO | WO 97/36538 | 10/1997 |
| WO | WO 97/49330 | 12/1997 |
| WO | WO 97/49330 A1 | 12/1997 |
| WO | WO 98/17174 A1 | 4/1998 |
| WO | WO9817174 A1 | 4/1998 |
| WO | WO 98/18382 | 5/1998 |
| WO | WO 98/43071 A1 | 10/1998 |
| WO | WO 98/51212 A1 | 11/1998 |
| WO | WO 98/57577 A1 | 12/1998 |
| WO | WO 99/00053 | 1/1999 |
| WO | WO 99/32030 A1 | 7/1999 |
| WO | WO 99/47039 A1 | 9/1999 |
| WO | WO 99/63884 | 12/1999 |
| WO | WO 00/21438 A1 | 4/2000 |
| WO | WO 00/28888 A1 | 5/2000 |
| WO | WO 00/59374 A1 | 10/2000 |
| WO | WO 01/13790 | 3/2001 |
| WO | WO 01/17421 A1 | 3/2001 |
| WO | WO 01/47426 | 3/2001 |
| WO | WO 0116577 | 3/2001 |
| WO | WO 01/40776 A1 | 6/2001 |
| WO | WO 01/45553 A1 | 6/2001 |
| WO | WO 01/67946 | 9/2001 |
| WO | WO 01/76461 A1 | 10/2001 |
| WO | WO 02/14793 A3 | 2/2002 |
| WO | WO 02/35999 | 5/2002 |
| WO | WO 02/062213 | 8/2002 |
| WO | WO 02/074162 | 9/2002 |
| WO | WO 02/085202 | 10/2002 |
| WO | WO 03/000125 A1 | 1/2003 |
| WO | WO 03/001180 | 1/2003 |
| WO | WO 03/009750 A3 | 2/2003 |
| WO | WO 03/011127 A1 | 2/2003 |
| WO | WO 03/020129 | 3/2003 |
| WO | WO 03/039326 A3 | 5/2003 |
| WO | WO 03/063697 | 8/2003 |
| WO | WO 03/063697 A1 | 8/2003 |
| WO | WO 03/073924 A1 | 9/2003 |
| WO | WO 2004/000114 | 12/2003 |
| WO | WO 2004/006748 A3 | 1/2004 |
| WO | WO 2004/069046 | 8/2004 |
| WO | WO 2004/075746 A2 | 9/2004 |
| WO | WO 2005/002434 | 1/2005 |
| WO | WO 2005/009221 A2 | 2/2005 |
| WO | WO 2005/010567 A2 | 2/2005 |
| WO | WO 2005/010568 A3 | 2/2005 |
| WO | WO 2005/020120 A2 | 3/2005 |
| WO | WO 2005/065540 | 7/2005 |
| WO | WO 2006/104790 | 10/2006 |
| WO | WO2008035076 A2 | 3/2008 |

OTHER PUBLICATIONS

Lee, Jason C.S., et al., "Simultaneous Measurement of Percent Carboxyhemoglobin and Functional Oxygen Saturation," *IEEE Engineering in Medicine and Biology Society*, CH2770-6, vol. 89, pp. 1092-1093. (1989).

Bongard, Frederic S., et al., "Continuous Dual Oximetry in Surgical critical care—Indications and Limitations," *Annals of Surgery*, vol. 216, No. 1, pp. 60-68 (1992).

Analytical Spectral Devices, "Bringing Analytical NIR Solutions to the Real World," available at http://www.asdi.com/about-valueadded.asp (last visited on Sep. 11, 2007).

Wikipedia, "Near Infrared Spectroscopy," available at http://en.

wikipedia.org/wiki/Near_infrared_spectroscopy (last visited on Sep. 11, 2007).

Rheineck-Leyssius, Aart t., et al.; "Advanced Pulse Oximeter Signal Processing Technology Compared to Simple Averaging: I. Effect on Frequency of Alarms in the Operating Room," *Journal of clinical Anestesia*, vol. 11, pp. 192-195 (1990).

Zahar, N., et al.; "Automatic Feedback Control of Oxygen Therapy Using Pulse Oximetry," *Annual International Conference of the IEEE Engineering in Medicine and Biology Society*, vol. 13, No. 4, pp. 1614-1615 (1991).

Aoyagi, T., et al.; "Analysis of Motion Artifacts in Pulse Oximetry," *Japanese Society ME*, vol. 42, p. 20 (1993) (Article in Japanese—contains English summary of article).

Barreto, A.B., et al.; "Adaptive Cancelation of Motion artifact in Photoplethysmographic Blood Volume Pulse Measurements for Exercise Evaluation," *IEEE-EMBC and CMBEC—Theme 4: Signal Processing*, pp. 983-984 (1995).

Vincente, L.M., et al.; "Adaptive Pre-Processing of Photoplethysmographic Blood Volume Pulse Measurements," pp. 114-117 (1996).

Plummer, John L., et al.; "Identification of Movement Artifact by the Nellcor N-200 and N-3000 Pulse Oximeters," *Journal of clinical Monitoring*, vol. 13, pp. 109-113 (1997).

Barnum, P.T., et al.; "Novel Pulse Oximetry Technology Capable of Reliable Bradycardia Monitoring in the Neonate," *Respiratory Care*, vol. 42, No. 1, p. 1072 (Nov. 1997).

Poets, C. F., et al.; "Detection of movement artifact in recorded pulse oximeter saturation," *Eur. J. Pediatr.*; vol. 156, pp. 808-811 (1997).

Masin, Donald I., et al.; "Fetal Transmission Pulse Oximetry," *Proceedings 19th International Conference IEEE/EMBS*, Oct. 30-Nov. 2, 1997; pp. 2326-2329.

Block, Frank E., Jr., et al.; "Technology evaluation report: Obtaining pulse oximeter signals when the usual probe cannot be used," *International journal of clinical Monitoring and Computing*, vol. 14, pp. 23-28 (1997).

Nijland, Roel, et al.; "Validation of Reflectance Pulse Oximetry: An Evaluation of a new Sensor in Piglets," *Journal of Clinical Monitoring*, vol. 13, pp. 43-49 (1997).

Soto, Denise A.; "A Comparative Study of Pulse Oximeter Measurements: Digit Versus Earlobe," Master of Science Thesis, California State University Dominguez Hills, May 1997, 46 pgs.

Faisst, Karin, et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).

Izumi, Akio, et al.; "Accuracy and Utility of a New Reflectance Pulse Oximeter for Fetal Monitoring During Labor," *Journal of Clinical Monitoring*, vol. 13, pp. 103-108 (1997).

Mannheimer, Paul D., et al.; "Wavelength Selection for Low-Saturation Pulse Oximetry," *IEEE Transactions on Biomedical Engineering*, vol. 44, No. 3, pp. 148-158 (Mar. 1997).

"Smaller Product, Tighter Tolerances Pose Dispensing Challenges for Medical Device Manufacturer," *Adhesives Age*, pp. 40-41 (Oct. 1997).

Buschman, J.P., et al.; "Principles and Problems of Calibration of Fetal Oximeters," *Biomedizinische Technik*, vol. 42, pp. 265-266 (1997).

Pickett, John, et al.; "Pulse Oximetry and PPG Measurements in Plastic Surgery," *Proceedings—19th International Conference—IEEE/EMBS*, Chicago, Illinois, Oct. 30-Nov. 2, 1997, pp. 2330-2332.

Leahy, Martin J., et al.; "Sensor Validation in Biomedical Applications," *IFAC Modelling and Control in Biomedical Systems*, Warwick, UK; pp. 221-226 (1997).

Barreto, Armando B., et al.; "Adaptive LMS Delay Measurement in dual Blood Volume Pulse Signals for Non-Invasive Monitoring," *IEEE*, pp. 117-120 (1997).

Crilly, Paul B., et al.; "An Integrated Pulse Oximeter System for Telemedicine Applications," *IEEE Instrumentation and Measurement Technology Conference*, Ottawa, Canada; May 19-21, 1997; pp. 102-104.

DeKock, Marc; "Pulse Oximetry Probe Adhesive Disks: a Potential for Infant Aspiration," *Anesthesiology*, vol. 89, pp. 1603-1604 (1998).

East, Christine E., et al.; "Fetal Oxygen Saturation and Uterine Contractions During Labor," *American Journal of Perinatology*, vol. 15, No. 6, pp. 345-349 (Jun. 1998).

Rhee, Sokwoo, et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, vol. 20, No. 4, pp. 1906-1909 (Oct. 1998).

Yang, Boo-Ho, et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.

König, Volker, et al.; "Reflectance Pulse Oximetry—Principles and Obstetric Application in the Zurich System," *Journal of Clinical Monitoring and Computing*, vol. 14, pp. 403-412 (1998).

Nogawa, Masamichi, et al.; "A Novel Hybrid Reflectance Pulse Oximater Sensor with improved Linearity and General Applicability to Various Portions of the Body," *Proceedings of the 20th Annual International Conference of the IEEE Engineering in Medicine and Biology Society*, vol. 20, No. 4, pp. 1858-1861 (1998).

Hayes, Matthew J., et al.; "Quantitative evaluation of photoplethysmographic artifact reduction for pulse oximetry," *SPIE*, vol. 3570, pp. 138-147 (Sep. 1998).

Edrich, Thomas, et al.; "Can the Blood Content of the Tissues be Determined Optically During Pulse Oximetry Without Knowledge of the Oxygen Saturation?—An In-Vitro Investigation," *Proceedings of the 20th Annual International conference of the IEEE Engineering in Medicine and Biology Society*, vol. 20, No. 6, pp. 3072-3075 (1998).

Hayes, Matthew J., et al.; "Artifact reduction in photoplethysmography," *Applied Optics*, vol. 37, No. 31, pp. 7437-7446 (Nov. 1998).

Such, Hans Olaf; "Optoelectronic Non-invasive Vascular Diagnostics Using multiple Wavelength and Imaging Approach," *Dissertation*, (1998).

Lutter, N., et al.; "Comparison of Different Evaluation Methods for a Multi-wavelength Pulse Oximeter," *Biomedizinische Technik*, vol. 43, (1998).

Ferrell, T.L., et al.; "Medical Telesensors," *SPIE*, vol. 3253, pp. 193-198 (1998).

Todd, Bryan, et al.; "The Identification of Peaks in Physiological Signals," *Computers and Biomedical Research*, vol. 32, pp. 322-335 (1999).

Rhee, Sokwoo, et al.; "Design of a Artifact-Free Wearable Plethysmorgraphic Sensor," *Proceedings of the First joint BMES/EMBS Conference*, Oct. 13-16, 1999, Altanta, Georgia, p. 786.

Rohling, Roman, et al.; "Clinical Investigation of a New Combined Pulse Oximetry and Carbon Dioxide Tension Sensor in Adult Anaesthesia," *Journal o Clinical Monitoring and Computing*, vol. 15; pp. 23-27 (1999).

Ikeda, Kenji, et al.; "Improvement of Photo-Electric Plethysmograph Applying Newly Developed Opto-Electronic Devices," *IEEE Tencon*, pp. 1109-1112 (1999).

Kaestle, S.; "An Algorithm for Reliable Processing of Pulse Oximetry Signals Under strong Noise Conditions," *Dissertation Book*, Lubeck University, Germany (1999).

Seelbach-Göbel, Birgit, et al.; "The prediction of fetal acidosis by means of intrapartum fetal pulse oximetry," *Am J. Obstet. Gynecol.*, vol. 180, No. 1, Part 1, pp. 73-81 (1999).

Yang, Boo-Ho, et al.; "Development of the ring sensor for healthcare automation," *Robotics and Autonomous Systems*, vol. 30, pp. 273-281 (2000).

Rhee, Sokwoo, et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.

Rhee, Sokwoo, et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois, Jul. 23-28, 2000; pp. 2796-2799.

Vicenzi, Martin N.; "Transesophageal versus surface pulse oximetry in intensive care unit patients," *Crit. Care Med.*; vol. 28, No. 7, pp. 2268-2270 (2000).

Goldman, Julian M.; "Masimo Signal Extraction Pulse Oximetry," *Journal of Clinical Monitoring and Computing*, vol. 16, pp. 475-483 (2000).

Coetzee, Frans M.; "Noise-Resistant Pulse Oximetry Using a Synthetic Reference Signal," *IEEE Transactions on Biomedical Engineering*, vol. 47, No. 8, Aug. 2000, pp. 1018-1026.

Nilsson, Lena, et al.; "Monitoring of Respiratory Rate in Postoperative Care Using a New Photoplethysmographic Technique," *Journal of Clinical Monitoring and Computing*, vol. 16, pp. 309-315 (2000).

Nijland, Mark J.M., et al.; "Assessment of fetal scalp oxygen saturation determination in the sheep by transmission pulse oximetry," *Am. J. Obstet Gynecol.*, vol. 183, No. 6, pp. 1549-1553 (Dec. 2000).

Edrich, Thomas, et al.; "Pulse Oximetry: An Improved In Vitro Model that Reduces Blood Flow-Related Artifacts," *IEEE Transactions on Biomedical Engineering*, vol. 47, No. 3, pp. 338-343 (Mar. 2000).

Schulz, Christian Eric; "Design of a Pulse Oximetry Sensor Housing Assembly," California State University Master's Thesis, *UMI Dissertation Services*, UMI No. 1401306, (May 2000) 63 pages.

Yao, Jianchu, et al.; "Design of a Plug-and-Play Pulse Oximeter," *Proceedings of the Second Joint EMBS/BMES Conference*, Houston, Texas, Oct. 23-26, 2002; pp. 1752-1753.

Aoyagi, T., et al.; "Pulse Oximeters: background, present and future," *Neonatal Care*, vol. 13, No. 7, pp. 21-27 (2000) (Article in Japanese—contains English summary of article).

Yokota, Nakaura, Takahashi, et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary of article).

Kaestle, S.; "Determining Artefact Sensitivity of New Pulse Oximeters in Laboratory Using Signals Obtained from Patient," *Biomedizinische Technik*, vol. 45 (2000).

Cubeddu, Rinaldo, et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).

Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).

Cysewska-Sobusaik, Anna; "Metrological Problems With noninvasive Transillumination of Living Tissues," *Proceedings of SPIE*, vol. 4515, pp. 15-24 (2001).

Rhee, Sokwoo, et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).

Belal, Suliman Yousef, et al.; "A fuzzy system for detecting distorted plethysmogram pulses in neonates and paediatric patients," *Physiol. Meas.*, vol. 22, pp. 397-412 (2001).

Hayes, Matthew J., et al.; "A New Method for Pulse Oximetry Possessing Inherent Insensitivity to Artifact," *IEEE Transactions on Biomedical Engineering*, vol. 48, No. 4, pp. 452-461 (Apr. 2001).

Gosney, S., et al.; "An alternative position for the pulse oximeter probe," *Anaesthesia*, vol. 56, p. 493 (2001).

Silva, Sonnia Maria Lopez, et al.; "NIR transmittance pulse oximetry system with laser diodes," *Clinical Diagnostic Systems, Proceedings of SPIE*, vol. 4255, pp. 80-87 (2001).

Maletras, Francois-Xavier, et al.; "Construction and calibration of a new design of Fiber Optic Respiratory Plethysmograph (FORP)," *Optomechanical Design and Engineering, Proceedings of SPIE*, vol. 4444, pp. 285-293 (2001).

Earthrowl-Gould, T., et al.; "Chest and abdominal surface motion measurement for continuous monitoring of respiratory function," *Proc. Instn Mech Engrs*, V215, Part H; pp. 515-520 (2001).

Gehring, Harmut, et al.; "The Effects of Motion Artifact and Low Perfusion on the Performance of a New Generation of Pulse Oximeters in Volunteers Undergoing Hypoxemia," *Respiratory Care*, Vol. 47, No. 1, pp. 48-60 (Jan. 2002).

Jopling, Michae W., et al.; "Issues in the Laboratory Evaluation of Pulse Oximeter Performance," *Anesth Analg*, vol. 94, pp. S62-S68 (2002).

Gostt, R., et al.; "Pulse Oximetry Artifact Recognition Algorithm for Computerized Anaesthetic Records," *Journal of Clinical Monitoring and Computing Abstracts*, p. 471 (2002).

Chan, K.W., et al.; "17.3: Adaptive Reduction of Motion Artifact from Photoplethysmographic Recordings using a Variable Step-Size LMS Filter," *IEEE*, pp. 1343-1346 (2002).

Relente, A.R., et al.; "Characterization and Adaptive Filtering of Motion Artifacts in Pulse Oximetry using Accelerometers," *Proceedings of the Second joint EMBS/BMES Conference*, Houston, Texas, Oct. 23-26, 2002; pp. 1769-1770.

Yamaya, Yoshiki, et al.; "Validity of pulse oximetry during maximal exercise in normoxia, hypoxia, and hyperoxia," *J Appl. Physiol.*, vol. 92, pp. 162-168 (2002).

Lutter, Norbert O., et al.; "False Alarm Rates of Three Third-Generation Pulse Oximeters in PACU, ICU and IABP Patients," *Anesth Analg*, vol. 94, pp. S69-S75 (2002).

Lutter, N., et al.; "Accuracy of Noninvasive Continuous Blood Pressure; Measurement Utilising the Pulse Transit Time," *Journal of clinical Monitoring and Computing*, vol. 17, Nos. 7-8, p. 469 (2002).

Liu, Ying, et al.; "Sensor design of new type reflectance pulse oximetry," *Optics in Health Care and Biomedical Optics: Diagnostics and Treatment, Proceedings of SPIE*, vol. 4916, pp. 98-102 (2002).

Kyriacou, Panayiotis A., et al.; "Esophageal Pulse Oximetry Utilizing Reflectance Photoplethysmography," *IEEE Transactions on Biomedical Engineering*, vol. 49, No. 11, pp. 1360-1368 (Nov. 2002).

Kyriacou, P. A., et al.; "Investication of oesophageal photoplethysmographic signals and blood oxygen saturation measurements in cardiothoracic surgery patients," *Physiological Measurement*, vol. 23, No. 3, pp. 533-545 (Aug. 2002).

Tobata, H., et al.; "Study of Ambient Light Affecting Pulse Oximeter Probes," *Ikigaku (Medical Technology)*, vol. 71, No. 10, pp. 475-476 (2002) (Article in Japanese—contains English summary of article).

Irie, A., et al.; "Respiration Monitors—Pulse Oximeters," *Neonatal Care*, vol. 15, No. 12, pp. 78-83 (2002) (Article in Japanese—contains English summary of article).

Koga, I., et al.; "Sigmoid colonic reflectance pulse oximetry and tonometry in a porcine experimental hypoperfusion shock model," *Acta Anaesthesiol Scand*, vol. 46, pp. 1212-1216 (2002).

Shaltis, Phillip, et al.; "Implementation and Validation of a Power-Efficient, High-Speed Modulation Design for Wireless Oxygen Saturation Measurement Systems," *IEEE*, pp. 193-194 (2002).

Warren, Steve, et al.; "Wearable Sensors and Component-Based Design for Home Health Care," *Proceedings of the Second Joint EMBS/BMES Conference*, Houston, Texas; Oct. 23-26, 2002; pp. 1871-1872.

Ericson, M.N., et al.; "In vivo application of a minimally invasive oximetry based perfusion sensor," *Proceedings of the Second Joint EMBS/BMES Conference*, Houston, Texas; Oct. 23-26, 2002, pp. 1789-1790.

Yoon, Gilwon, et al.; "Multiple diagnosis based on Photoplethysmography: hematocrib, SpO2, pulse and respiration," *Optics in Health Care and Biomedical optics: Diagnostics and Treatment; Proceedings of the SPIE*, vol. 4916; pp. 185-188 (2002).

Hase, Kentaro, et al.; "Continuous Measurement of Blood Oxygen Pressure Using a Fiber Optic Sensor Based on Phosphorescense Quenching," *Proceedings of the Second Joint EMBS/BMES Conference*, Houston, Texas; Oct. 23-26, 2002, pp. 1777-1778.

Pothisam, W., et al.; "A non-invasive hemoglobin measurement based pulse oximetry," *Optics in Health Care and Biomedical Optics: Diagnostics and Treatment; Proceedings of SPIE*, vol. 4916; pp. 498-504 (2002).

Tremper, K.K.; "A Second Generation Technique for Evaluating Accuracy and Reliability of Second Generation Pulse Oximeters," *Journal of Clinical Monitoring and Computing*, vol. 16, pp. 473-474 (2002).

Silva, Sonnia Maria Lopez, et al.; "Near-infrared transmittance pulse oximetry with laser diodes," *Journal of Biomedical Optics*, vol. 8, No. 3, pp. 525-533 (Jul. 2003).

Cyrill, D., et al.; "Adaptive Comb Filter for Quasi-Periodic Physiologic Signals," *Proceedings of the 25th Annual International Conference of the IEEE EMBS*, Cancun, Mexico, Sep. 17-21, 2003; pp. 2439-2442.

Matthews, Nora S. et al.; "An evaluation of pulse oximeters in dogs, cats and horses," *Veterinary Anaesthesia and Analgesia*, vol. 30, pp. 3-14 (2003).

Stetson, Paul F.; "Determining Heart Rate from Noisey Pulse Oximeter Signals Using Fuzzy Logic," *The IEEE International Conference on Fuzzy Systems*, St. Louis, Missouri, May 25-28, 2003; pp. 1053-1058.

Aoyagi, Takuo; "Pulse oximetry: its invention, theory, and future," *Journal of Anesthesia*, vol. 17, pp. 259-266 (2003).

Avidan, A.; "Pulse oximeter ear probe," *Anaesthesia*, vol. 58, pp. 726 (2003).

Lee, C.M., et al.; "Reduction of motion artifacts from photoplethysmographic recordings using wavelet denoising approach," *IEEE EMBS Asian-Pacific Conference on Biomedical Engineering*, Oct. 20-22, 2003; pp. 194-195.

Mendelson, Y., et al.; "Measurement Site and Photodetector Size Considerations in Optimizing Power Consumption of a Wearable Reflectance Pulse Oximeter," *Proceedings of the 25th Annual International conference of the IEEE EMBS*, Cancun, Mexico, Sep. 17-21, 2003; pp. 3016-3019.

Itoh, K., et al.; "Pulse Oximeter," *Toyaku Zasshi* (Toyaku Journal), vol. 25, No. 8, pp. 50-54 (2003) (Article in Japanese—contains English summary of article).

Matsui, A., et al.; "Pulse Oximeter," *Neonatal Care*, vol. 16, No. 3, pp. 38-45 (2003) (Article in Japanese—contains English summary of article).

Nakagawa, M., et al.; "Oxygen Saturation Monitor," *Neonatal Monitoring*, vol. 26, No. 5, pp. 536-539 (2003) (Article in Japanese—contains English summary of article).

Kubota, H., et al.; "Simultaneous Monitoring of PtcCO2 and SpO2 using a Miniature earlobe sensor," *Jinko Kokyo* (*Aritificial Respiration*), vol. 20, No. 1, pp. 24-29 (2003).

Lebak, J.W., et al.; "Implementation of a Standards-Based Pulse Oximeter on a Wearable, Embedded Platform," *Proceeding of the 25th Annual International Conference of the IEEE EMBS*, Cancun, Mexico, Sep. 17-21, 2003; pp. 3196-3198.

Nagl, L., et al.; "Wearable Sensor System for Wireless State-of-Health Determination in Cattle," *Proceeding of the 25th Annual International Conference of the IEEE EMBS*, Cancun, Mexico, Sep. 17-21, 2003; pp. 3012-3015.

Östmark, Åke, et al.; "Mobile Medical Applications Made Feasible Through Use of EIS Platforms," *IMTC—Instrumentation and Measurement Technology Conference*, Vail, Colorado; May 20-22, 2003; pp. 292-295.

Warren, Steve, et al.; "A Distributed Infrastructure for Veterinary Telemedicine," *Proceedings of the 25th Annual International Conference of the IEEE EMBS*, Cancun, Mexico; Sep. 17-21, 2003; pp. 1394-1397.

Pujary, C., et al.; "Photodetector Size Considerations in the Design of a Noninvasive Reflectance Pulse Oximeter for Telemedicine Applications," *IEEE*, pp. 148-149 (2003).

A. Johansson; "Neural network for photoplethysmographic respiratory rate monitoring," *Medical & Biological Engineering & Computing*, vol. 41, pp. 242-248 (2003).

Reuss, James L.; "Factors Influencing Fetal Pulse Oximetry Performance," *Journal of clinical Monitoring and Computing*, vol. 18, pp. 13-14 (2004).

Mannheimer, Paul D., et al.; "The influence of Larger Subcutaneous Blood Vessels on Pulse Oximetry," *Journal of clinical Monitoring and Computing*, vol. 18, pp. 179-188 (2004).

Wendelken, Suzanne, et al.; "The Feasibility of Using a Forehead Reflectance Pulse Oximeter for Automated Remote Triage," *IEEE*, pp. 180-181 (2004).

Lopez-Silva, S.M., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.

Sugino, Shigekzau, et al.; "Forehead is as sensitive as finger pulse oximetry during general anesthesia," *Can J. Anesth.; General Anesthesia*, vol. 51, No. 5; pp. 432-436 (2004).

Addison, Paul S., et al.; "A novel time-frequency-based 3D Lissajous figure method and its application to the determination of oxygen saturation from the photoplethysmogram," *Institute of Physic Publishing, Meas. Sci. Technol.*, vol. 15, pp. L15-L18 (2004).

Jovanov, E., et al.; "Reconfigurable intelligent Sensors for Health Monitoring: A case Study of Pulse Oximeter Sensor," *Proceedings o the 26th Annual International conference of the IEEE EMBS*, San Francisco, California, Sep. 1-5, 2004, pp. 4759-4762.

Kocher, Serge, et al.; "Performance of a Digital $PCO_2$/$SPO_2$ Ear Sensor," *Journal of Clinical Monitoring and Computing*, vol. 18, pp. 75-59 (2004).

Yao, Jianchu, et al.; "A Novel Algorithm to Separate Motion Artifacts from Photoplethysmographic Signals Obtained With a Reflectance Pulse Oximeter," *Proceedings of the 26th Annual International conference of the IEEE EMBS*, San Francisco, California, Sep. 1-5, 2004; pp. 2153-2156.

Nuhr, M., et al.: "Forehead $SpO_2$ monitoring compared to finger $SpO_2$ recording in emergency transport," *Anaesthesia*, vol. 59, pp. 390-393 (2004).

Johnston, William S., et al.; "Effects of Motion Artifacts on helmet-Mounted Pulse Oximeter Sensors," 2 pgs. (2004).

Branche, Paul C., et al.; "Measurement Reproducibility and Sensor Placement Considerations in Designing a Wearable Pulse Oximeter for Military Applications," 2 pgs. (2004).

Kocher, Serge, et al.; "Performance of a Digital $PCO_2$/$SPO_2$ Ear Sensor," *Journal of Clinical Monitoring and Computing*, vol. 18, pp. 75-79 (2004).

ISR/PCTUS2008/003182; Date of mailing: Jun. 30, 2008.

Heuss, Ludwig T., et al.; "Combined Pulse Oximetry / Cutaneous Carbon dioxide Tension Monitoring During Colonoscopies: Pilot study with a Smart Ear Clip," *Digestion*, vol. 70, pp. 152-158 (2004).

Matsuzawa, Y., et al.; "Pulse Oximeter," *Home Care Medicine*, pp. 42-45 (Jul. 2004); (Article in Japanese—contains English summary of article).

Crespi, F., et al.; "Near infrared oxymeter prototype for non-invasive analysis of rat brain oxygenation," *Optical Sensing, Proceedings of SPIE*, vol. 5459, pp. 38-45 (2004).

Johnston, W.S. et al.; "Extracting Breathing Rate Information from a Wearable Reflective Pulse Oximeter Sensor," *Proceedings of the 26th Annual International conference of the IEEE EMBS*, San Francisco, California; Sep. 1-5, 2004; pp. 5388-5391.

Spigulis, Janis, et al.; "Optical multi-channel sensing of skin blood pulsations," *Optical Sensing, Proceedings of SPIE*, vol. 5459, pp. 46-53 (2004).

Yan, Yong-sheng, et al.; "Reduction of motion artifact in pulse oximetry by smoothed pseudo Wigner-Ville distribution," *Journal of NeuroEngineering and Rehabilitation*, vol. 2, No. 3 (9 pages) (Mar. 2005).

Urquhart, C., et al.; "Ear probe pulse oximeters and neonates," *Anaesthesia*, vol. 60, p. 294 (2005).

\* cited by examiner

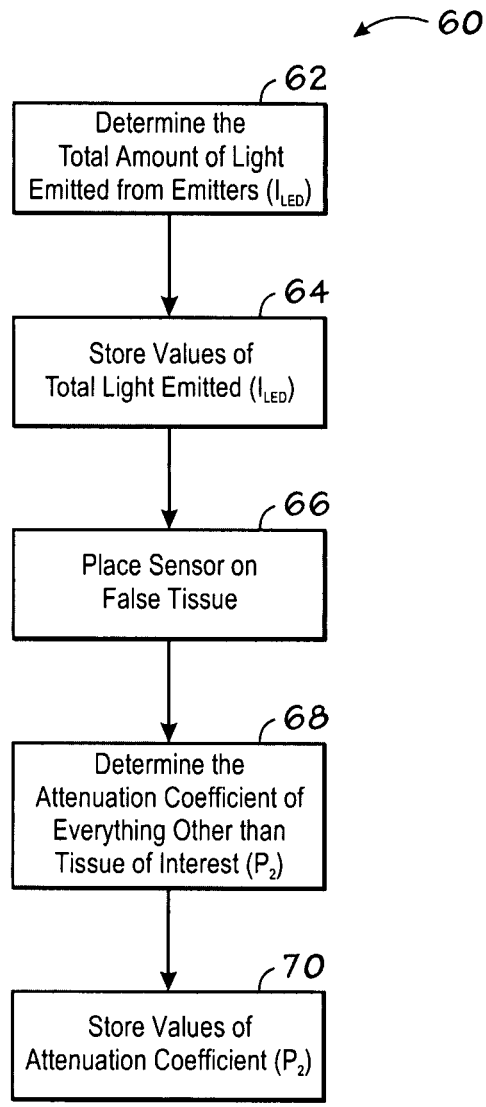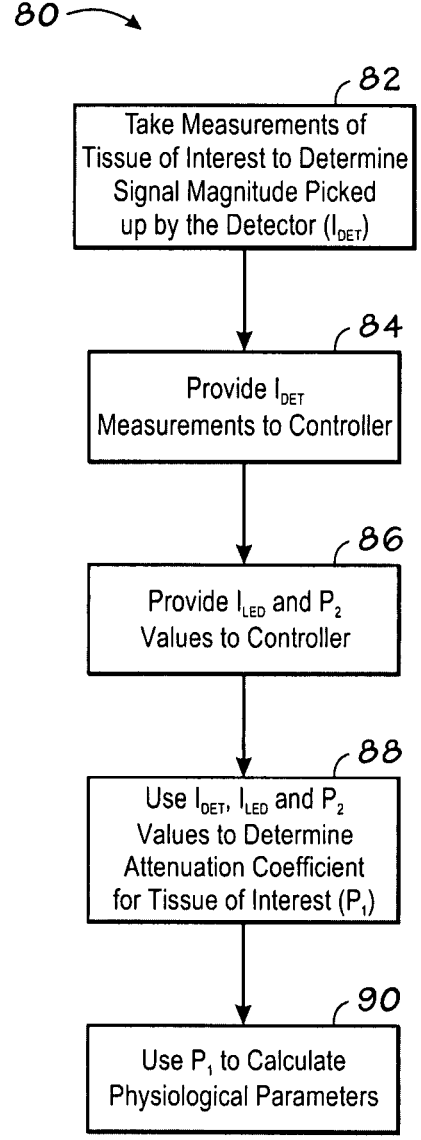
FIG. 4
FIG. 5

CANCELLATION OF LIGHT SHUNTING

TECHNICAL FIELD

The present invention relates generally to medical devices and, more particularly, to medical devices for non-invasively measuring physiological parameters of a patient.

BACKGROUND

This section is intended to introduce the reader to various aspects of art that may be related to various aspects of the present invention, which are described and/or claimed below. This discussion is believed to be helpful in providing the reader with background information to facilitate a better understanding of the various aspects of the present invention. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other health care personnel with the information they need to provide the best possible healthcare for their patients. As a result, such monitoring devices have become an indispensable part of modern medicine.

One technique for monitoring certain physiological characteristics of a patient is commonly referred to as pulse oximetry, and the devices built based upon pulse oximetry techniques are commonly referred to as pulse oximeters. Pulse oximetry may be used to measure various blood flow characteristics, such as the blood-oxygen saturation of hemoglobin in arterial blood, the volume of individual blood pulsations supplying the tissue, and/or the rate of blood pulsations corresponding to each heart beat of a patient. In fact, the "pulse" in pulse oximetry refers to the time varying amount of arterial blood in the tissue during each cardiac cycle.

Pulse oximeters typically utilize a non-invasive sensor that transmits electromagnetic radiation, such as light, through a patient's tissue and then photo-electrically detects the absorption and scattering of the transmitted light in such tissue. One or more of the above mentioned physiological characteristics may then be calculated based upon the amount of light absorbed and scattered. More specifically, the light passed through the tissue is typically selected to be of one or more wavelengths that may be absorbed and scattered by the blood in an amount correlative to the amount of blood constituent present in the tissue. The measured amount of light absorbed and scattered may then be used to estimate the amount of blood constituent in the tissue using various algorithms.

The pulse oximetry measurement depends in part on an assumption that the contribution of detected light that has not passed through a patient's tissue is negligible. This assumption, however, may not be accurate. Specifically, light shunting may occur, wherein light transmitted from an emitter in the sensor may arrive at a detector without first having traveled through the patient's tissue. The light shunting may cause measurement variations that do not relate to the amount of blood constituent and, therefore, may lead to inaccurate measurements.

SUMMARY

Certain aspects commensurate in scope with the originally claimed invention are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In accordance with one aspect of the present invention, there is provided a method of manufacture for a non-invasive sensor. The method includes providing a sensor communicatively coupled to a monitor, wherein the sensor is configured to emit and detect electromagnetic radiation. The method also includes determining a first signal value for each wavelength of light emitted from an emitter of the sensor and storing the first signal value in a memory. Additionally, the method includes placing false tissue on the sensor, operating the sensor to determine a second signal value for each wavelength emitted from the emitter of the sensor and storing the second signal value in the memory.

In accordance with another aspect of the present invention, there is provided a method for operating a system for non-invasively determining physiological parameters. The method includes using a sensor to take measurements of tissue of interest and providing the measurements to a controller in a monitor. Additionally, first and second values are retrieving from memory, the first value representing an amount of light emitted from emitters in the sensor and the second value representing an attenuation coefficient of everything other than the tissue of interest. A third value representing an attenuation coefficient for the tissue of interest is determined using the measurements provided to the controller and the first and second values. The third value is used to calculate physiological parameters.

In accordance with yet another aspect of the present invention, there is provided a system comprising a sensor and a monitor. The sensor includes an emitter configured to emit electromagnetic radiation at tissue and a detector configured to generate a signal in response to detecting the electromagnetic radiation emitted from the emitter. The monitor is communicatively coupled with the sensor and includes a controller configured to remove a shunting light value from the generated signal to produce an attenuation coefficient of the tissue. The monitor is configured to use the attenuation coefficient in calculating physiological parameters.

BRIEF DESCRIPTION OF THE DRAWINGS

Certain exemplary embodiments are described in the following detailed description and in reference to the drawings in which:

FIG. 4 is a flow chart illustrating a technique for calibrating the system of FIG. 1 in accordance with an exemplary embodiment of the present invention; and FIG. 5 is a flow chart representation of a method for canceling the effects of light shunting in the system of FIG. 1 in accordance with an exemplary embodiment of the present invention.

DETAILED DESCRIPTION

One or more specific embodiments of the present invention will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

In accordance with the present techniques, a system and method are provided for canceling shunted light. The method includes determining and storing a value representative of an amount of shunted light. The stored value is subsequently used to cancel all or a portion of the shunted light from a detected signal. The method may be implemented in systems using photoelectric sensors, such as pulse oximeters for example.

Figure 1:
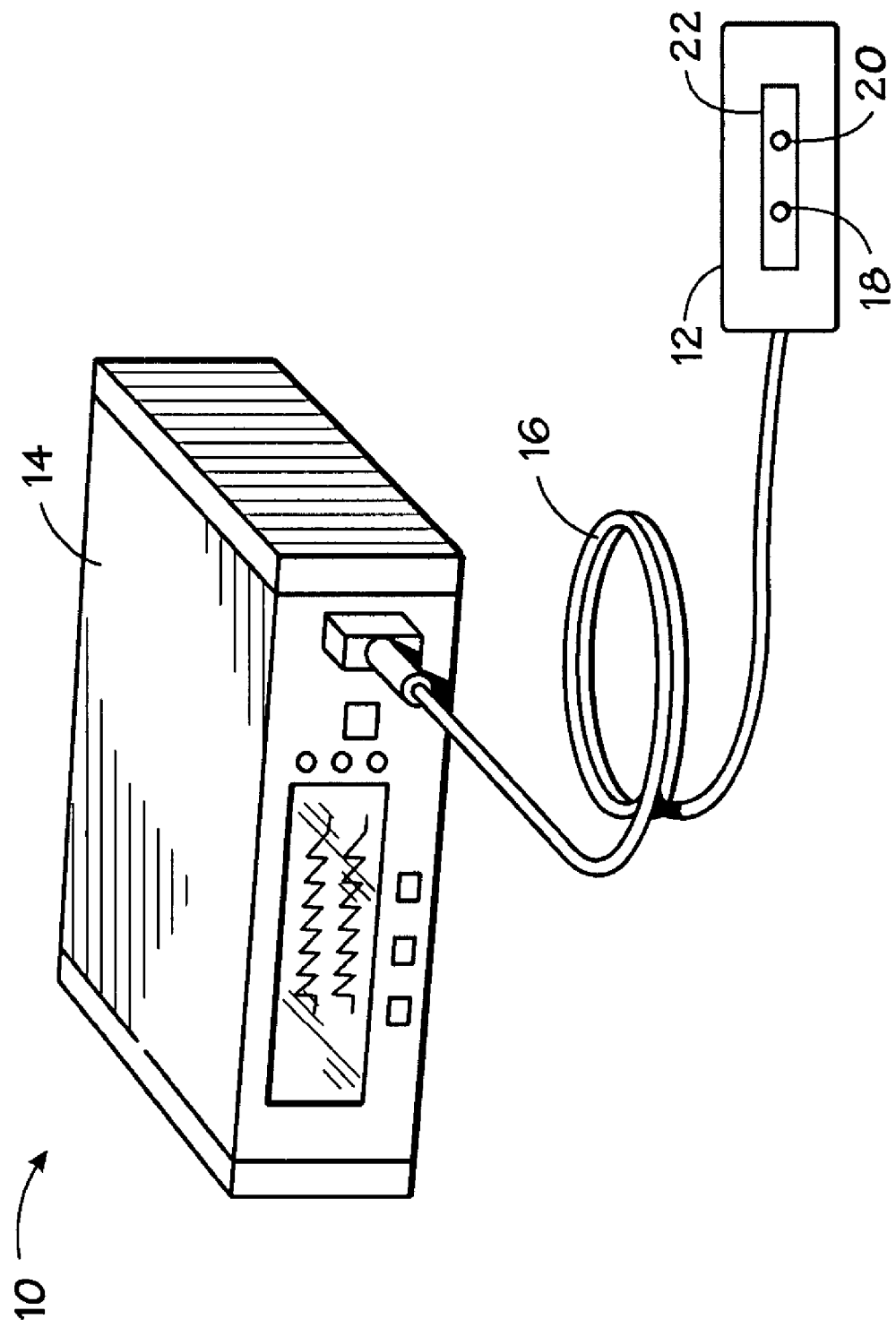
FIG. 1 illustrates a system for non-invasively determining physiological parameters in accordance with an exemplary embodiment of the present invention.

Turning to FIG. 1, a system for non-invasively determining physiological parameters is illustrated in accordance with an exemplary embodiment of the present invention and is generally designated by the reference numeral 10. The system 10 includes a sensor 12 coupled with a monitor 14 via a cable 16. The sensor 12 includes an emitter 18 and a detector 20. The emitter 18 may include one or more electromagnetic radiation sources such as a light emitting diodes (LEDs), an array of LEDs, a white light source, a tunable laser, or any other source that transmits electromagnetic radiation within a region of the electromagnetic spectrum useful for the determination of physiological parameters. The detector 20 may be a photosensitive diode, photosensitive transistor or other means for detecting electromagnetic radiation. The detector 20 is configured to detect electromagnetic radiation originating from the emitter 18.

The sensor 12 may be either a transmission-type sensor or a reflection-type sensor. In a transmission-type sensor, the sensor's emitter and detector lie on opposing sides of the tissue when the sensor is applied to a patient. The optical path of the light originating from the emitter 18 is substantially in-line with an imaginary axis connecting the emitter 18 and the detector 20. For reflectance-type sensors, the optical path is somewhat more complicated, as the light first enters perfused tissue and then is scattered back to the detector 20. In an exemplary embodiment, the sensor 12 is a reflectance type sensor, and the detector 20 and emitter 18 are mounted on a circuit board 22. Mounting the emitter 18 and the detector 20 on the same circuit board 22 allows for a constant geometric orientation between the emitter 18 and detector 20 to be maintained. For example, the circuit board 22 maintains the emitter 18 and detector 20 at a controlled optical distance relative to each other. The controlled optical distance reduces the amount of variance of light shunting during iterative measurements, to facilitate the approximation of and subsequent cancellation of the shunted light, as will be discussed in greater detail below.

Figure 2:
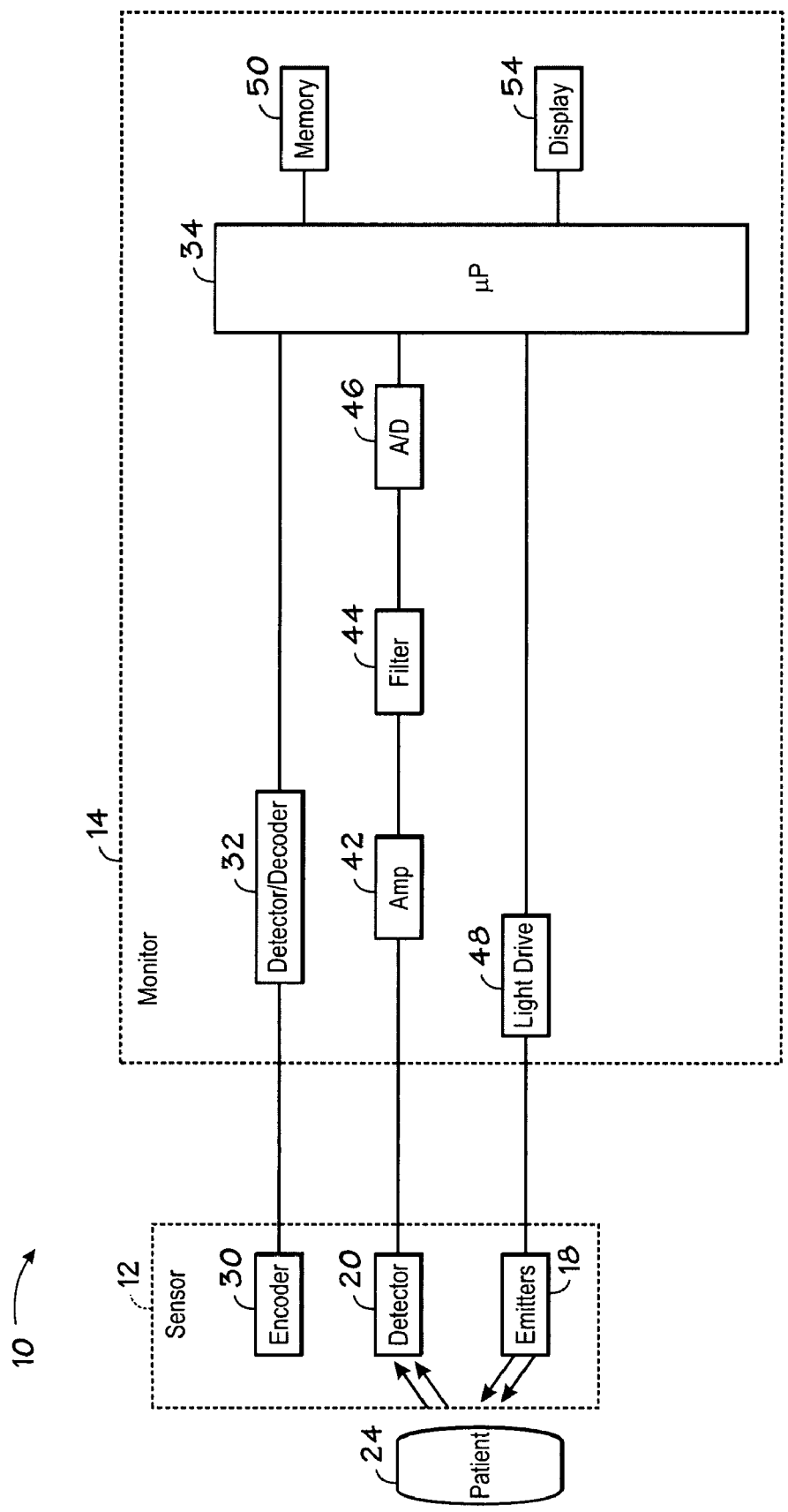
FIG. 2 is a block diagram of a sensor and a monitor of the system illustrated in FIG. 1 in accordance with an exemplary embodiment of the present invention.

Referring to FIG. 2, a block diagram of the system 10 of FIG. 1 is illustrated in accordance with an exemplary embodiment of the present invention. As can be seen, the sensor is configured so that the detector 20 receives light originating from the emitter 18 after it has passed through a patient's tissue 24. Additionally, the sensor 12 includes an encoder 30, which that may be a resistor having a value representative of operating characteristics of the sensor 12. In an alternative embodiment, the encoder 30 may be a memory device such as random access memory (RAM), a flash memory, a programmable read only memory (PROM), or an electrically erasable programmable read only memory (EEPROM), for example, configured to store values related to the shunting characteristics of the sensor 12. For example, the encoder 30 may store constants or coded values related to light shunting. Additionally, the encoder may be configured to store other parameters related to the particular sensor being used, such as the particular wavelengths at which the emitter 18 is operating, for example. As discussed in greater detail below, the stored constants or coded values may be used to cancel shunted light in order to achieve a more accurate measurement of the amount of light attenuation resulting from the tissue of interest.

The encoder 30 may be communicatively coupled to the monitor 14 in order to communicate the constant or coded values to a detector/decoder 32 in the monitor 14. The detector/decoder 32 is provided for reading the constants or coded values from the encoder 30 in the sensor 12. If the encoder stores constants, the constants may be provided directly to a controller 34 from the detector/decoder 32. Alternatively, if coded values are used, the detector/decoder 32 may correlate the coded values to constants using a look up table (not shown). In such a configuration, the look-up table may be configured to provide the corresponding constants to the controller 34.

The controller 34 may be a microprocessor configured to compute physiological parameters using algorithms known in the art. The constants are provided to the controller 34 for the determination of the amount of detected light that passed through the patient's tissue 24 during operation of the system 10. Specifically, the constants are used to remove an amount of shunted light from a detected signal so that the determination of physiological parameters does not include the shunted light, as will be discussed in greater detail below.

During use of the system 10, the controller 34 receives a signal representing the total amount of light detected from the sensor 12. This signal originates from the detector 20 generating an electrical current in response to the total light detected from the emitter 18, i.e., light that has passed through the tissue 24 and shunted light, and provides the generated signal to the monitor 14 for processing. The monitor 14 amplifies (amplifier 42) and filters (filter 44) the signal before converting (converter 46) the signal to a digital signal. The digital signal is provided to the controller 34 and used in conjunction with the stored constants discussed above to determine the amount of light attenuation of the tissue of interest. Once the light attenuation of the tissue of interest is calculated, by removing the shunted light from the detected signal, it may be used in computing the various physiological parameters in accordance with algorithms known in the art.

As illustrated in FIG. 2, additional component parts of the monitor 14 may include a light drive 48, a memory device 50, and a display 54. The light drive 48 drives the emitters 18 and the display 54 displays the physiological parameters once they are computed. The memory device 50 may be used to store the algorithms used in computing physiological parameters.

Figure 3:
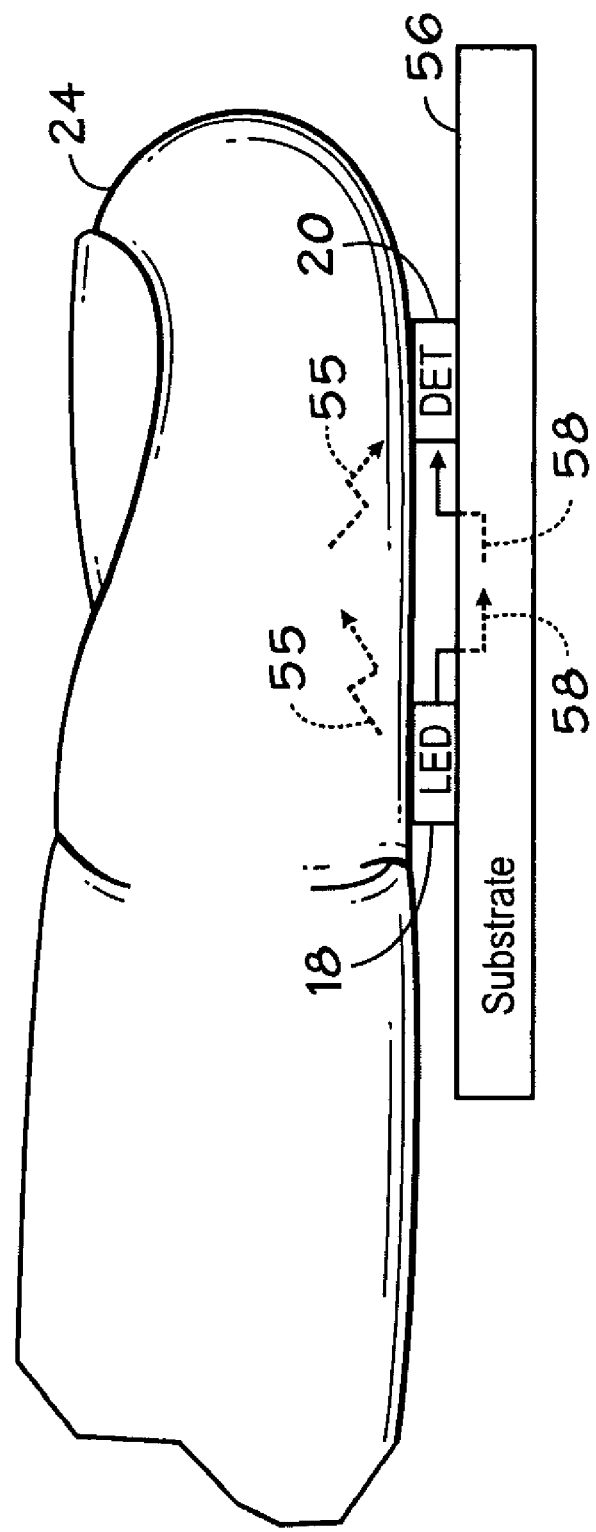
FIG. 3 illustrates possible light pathways for light to arrive at a detector from an emitter in the system of FIG. 1 in accordance with an exemplary embodiment of the present invention.

To demonstrate the effects of light shunting, a reflectance type sensor is illustrated in FIG. 3. Specifically, two possible pathways by which the light may travel from the emitter 18 to arrive at the detector 20 are illustrated. Ideally, all of the electromagnetic radiation from the emitter 18 arrives at the detector 20 after having passed through the tissue of interest 24, as indicated by the arrows 55. However, in practice, some of the light from the emitter 18 may be shunted through the circuit board 56 and may be detected by the detector 20 without having passed through the tissue of interest 24, as indicated by the arrows 58. The detected light that does not pass through the tissue of interest 24, i.e., the shunted light indicated by the arrows 58, may cause measurement errors in the parameters, e.g., oxygen saturation, calculated by the monitor 14.

For example, in one embodiment, the system 10 implemented may be an oximeter with a first light signal operating in the red region of the electromagnetic spectrum and the second light signal in the infrared region of the electromagnetic spectrum. The detected light signals are conditioned and processed to determine AC and DC signal components. Once obtained, the AC and DC components may be used to compute a modulation ratio of the red to infrared signals. The modulation ratio is generally referred to as "the ratio of ratios," or "Ratrat," and may be represented as:

$$Ratrat = \frac{AC_{Rd}/DC_{Rd}}{AC_{IR}/DC_{IR}}. \quad (1)$$

The Ratrat is used to calculate physiological parameters in accordance with algorithms known in the art. Among other things, shunted light causes the DC terms of a Ratrat equation to be artificially high. Accordingly, removal of the shunted light will help increase the accuracy of the parameters calculated based on signals received from the sensor 12.

To determine the amount of shunted light for a particular sensor, several parameters of the particular sensor or sensor family can be evaluated. The parameters may include, for example, the signal magnitude emitted from the emitter 18 and the signal magnitude detected by the detector 20. The signal magnitude detected by the detector 20 while the sensor 12 is in service represents the sum of the light that passed through the tissue of interest 24 and the shunted light. As such, the total light detected by the detector 20 can be represented by:

$$I_{DET} = I_{LED} P_1 + I_{LED} P_2, \quad (2)$$

where $I_{DET}$ represents the signal magnitude picked up by the detector, and $I_{LED}$ represents the signal magnitude from the emitters 18. $P_1$ represents the attenuation coefficient of the tissue of interest, as discussed above, and resulting from light traversing tissue as shown by arrows 55 in FIG. 3. $P_2$ represents the attenuation coefficient of everything other than the tissue of interest resulting from shunted light, as shown by arrows 58 in FIG. 3. The parameter that system 10 may use in determining physiological parameters is $P_1$, the attenuation of the tissue of interest or the attenuation coefficient of light in a capillary bed. Once the $P_1$ value has been determined, the AC and DC values of the Ratrat equation (1) may be determined based on the $P_1$ value. Accordingly, equation (2) may be rearranged to solve for $P_1$.

$$P_1 = \frac{I_{DET} - I_{LED} P_2}{I_{LED}}. \quad (3)$$

The value of $P_2$ can be determined by taking measurements of only the shunted light before the sensor is placed into service. A flow chart illustrating a technique 60 for use in determining an amount of light shunting ($P_2$) for the system 10 of FIG. 1 is shown in accordance with an exemplary embodiment of the present invention. The technique 60 may be used during the manufacture or testing of the system 10 or, alternatively, prior to the manufacture of the system 10. Additionally, the technique 60 may be performed for each sensor or for each type of sensor depending on the controls of the manufacturing process involved. For example, if the controls are tight, meaning there is only slight variance between sensors, then the technique may be performed on only a small sample size of sensors and the results may be reasonably accurate for all other sensors of that type.

The technique 60 begins with a determination of the total amount of light emitted from the emitters ($I_{LED}$), as indicated at block 62. The determined $I_{LED}$ values are then stored, as indicated at block 64. The attenuation coefficient of everything other than the tissue of interest ($P_2$) is then determined by placing false tissue on the sensor and taking measurements, as indicated at blocks 66 and 68. The $P_2$ values are stored for later use in canceling the light shunting from a measured signal, as indicated at block 70. The $P_2$ signal measured at the detector while the false tissue is in place represents the amount of shunted light for that sensor.

The technique 60 may be performed using a testing device (not shown) configured to operate the sensor 12 to determine the various operating parameters. The false tissue may be a false finger or other tissue phantom, made of black foam or black Acrylonitrile Butadiene Styrene (ABS) plastic, for example. The false tissue should be opaque so that it does not allow light that has been directed into it from the emitter 18 to be reflected back to the detector 20. Specifically, the false tissue should absorb the light that impinges on it so that any signal detected by the detector 20 may be attributed to shunting. More sophisticated embodiments of false tissue are possible. For instance, the surface of the false tissue could have optical properties similar to real tissue so that light reflected off the surface is reflected back into the sensor substrate and is included in the shunted light measurement.

As mentioned above, a small sample size for a given type of sensor may be representative of all sensors of that type such that averaged $P_2$ and $I_{LED}$ values from the samples may be used in all sensors of that particular type having the same particular configuration, thus saving resources during manufacturing. Specifically, as the actual amount of light shunting that occurs while using a particular sensor may vary from user-to-user, exactness in the $P_2$ and $I_{LED}$ values for that particular sensor is not necessary. Indeed, averaged $P_2$ and $I_{LED}$ values provide adequate cancellation of shunted light to allow for increased accuracy in measurements. As such, an average $P_2$ and $I_{LED}$ values can be representative for an entire type or family of sensors. In this situation, where $P_2$ values are provided based on sensor type, the monitor 14 can store the values for each type of sensor without reading values from each sensor. As discussed above, the monitor may recognize a sensor when the sensor is coupled to the monitor, so the monitor can automatically retrieve the appropriate constants for cancellation of the shunted light.

The approximation of light shunting should be performed separately for each wavelength of light at which measurements are to be taken. For example, for a sensor having LEDs operating in both the red region the infrared region of the electromagnetic spectrum, the calculation may be done separately for each LED and a $P_2$ value is determined for each LED.

The constants or coded values stored on the sensor 12 or the monitor 14 related to shunted light may include the $P_2$ and $I_{LED}$ values. The parameter $I_{DET}$ is determined during operation of the sensor 12 and the parameter $P_1$ is calculated in accordance with equation (3). $I_{LED}$ values may also be determined during operation, so that only the $P_2$ values are stored in memory prior to operation of the sensor. $I_{LED}$ values are usually controlled by the instrument to adapt to differences between different patients. There is usually a large variation in optical properties from one patient to the next, so the light output of the emitters is adjusted by the instrument in order to keep the signal at the detector within a useful range. The calculated $P_1$ values, once determined, may be used for calculating physiological parameters in accordance with algorithms known in the art.

It should be understood that the amount of shunting that actually occurs may depend on many factors, one of which is the type of sensor being used. An estimation of the amount of shunted light is sufficiently accurate as long as the sensor materials and the optical distance between the emitter 18 and detector 20 remain relatively constant (i.e. controlled optical distance). Specifically, although there may be variance in the amount of shunted light due to patient specific factors, variation in the amount of shunted light resulting from sensor specific factors can be limited by limiting variance from one sensor to another for a particular sensor type.

Additionally, the amount of light shunting may vary among various sensors. Indeed, particular sensors may be more susceptible to shunting. For example, sensors implementing a white bandage to secure the sensor 12 to the tissue of interest, or sensors where the circuit board 22 is translucent, may be especially vulnerable to shunting. Furthermore, for example, if the material used to manufacture a particular type of sensor changes, the amount of shunted light may change and the constant or coded values may no longer be accurate. As such, the above mentioned $P_2$ parameter will vary according to each specific sensor design and values should be determined for each particular sensor design.

As mentioned above, the estimated amount of shunted light can be stored as a constant or as a coded value in the encoder 30 of the sensor 12 shown in FIG. 2. The constant or coded value may be communicated to the monitor 14 when the sensor 12 is used in conjunction with a monitor 14. The communication of constants or coded values from a sensor to a monitor is described in U.S. Pat. No. 6,628,975, which is incorporated herein by reference. In an alternative embodiment, the constant or coded values may be stored in a look-up table of the monitor 14. The sensor 12 communicates the coded values to the monitor 14 and the coded values are correlated with the appropriate constants stored in the look-up table. In yet another alternative embodiment, the monitor 14 may store constants for multiple sensor types and upon coupling of the sensor 12 to the monitor 14, the monitor 14 determines what particular sensor is being used and retrieves the corresponding constants for that particular sensor.

As described above, the constants and/or coded values are used to indicate a shunted light value that is representative of the amount of shunted light that can be expected to occur for a particular sensor or for a particular sensor type. Knowing the amount of shunted light, the monitor 14 can remove the shunted light from the detected light signal to determine the amount of light attenuation of the tissue of interest ($P_1$ values). The $P_1$ values can then be used to in determining the AC and DC values representative of only the portion of the detected signal that can be attributed to light that has traversed the tissue of interest.

Turning to FIG. 5, a flow chart representation of a technique 80 for cancellation of light shunting during operation of the system 10 of FIG. 1 is illustrated. The technique 80 includes taking measurements of tissue using the non-invasive sensor 12 to determine the signal magnitude picked up by the detector ($I_{DET}$), as indicated at block 82. The $I_{DET}$ measurements are provided to the controller 38, as indicated at block 84. The stored values, $I_{LED}$ and $P_2$, are provided to the controller 38, as indicated at block 86. The $I_{DET}$, $I_{LED}$, and $P_2$ values are then used to determine the attenuation coefficient for tissue of interest ($P_1$), as indicated at block 88, by canceling the shunted light using equation (3). Physiological parameters may then determined using the value $P_1$, as indicated at block 90. Specifically, in the case of a pulse oximeter, the Ratrat may be determined using the $P_1$ values to determine the AC and DC parts of the detected signal.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method of manufacture for a non-invasive sensor comprising:
   communicatively coupling a sensor to a test device, wherein the sensor is configured to emit and detect electromagnetic radiation;
   determining a first signal value for each wavelength of light emitted from an emitter of the sensor;
   storing the first signal value in a memory;
   placing the sensor on a false tissue, the false tissue being opaque;
   operating the sensor to determine a second signal value for each wavelength emitted from the emitter of the sensor while the sensor is placed on the false tissue; and
   storing the second signal value in the memory.

2. The method of claim 1, wherein the first signal value is representative of a total amount of light emitted from the emitter of the sensor ($I_{LED}$) and the second signal value is representative of the attenuation coefficient of everything other than tissue of interest ($P_2$).

3. The method of claim 1 wherein the memory is in the sensor.

4. The method of claim 1 wherein the memory is in a monitor.

5. The method of claim 4 comprising storing coded values in a memory of the sensor, wherein the coded values correlate with the first and second values stored in the memory of the monitor.

6. The method of claim 1 wherein providing a sensor comprises providing an emitter and a detector having a controlled optical distance.

7. The method of claim 6 wherein the emitter and detector are mounted on a common circuit board.

8. A method for operating a system for non-invasively determining physiological parameters, the method comprising:
   using a sensor to take measurements of tissue of interest;
   providing the measurements to a controller in a monitor;
   retrieving from a memory a first value and a second value, the first value representing an amount of light emitted from emitters in the sensor and the second value representing an attenuation coefficient of everything other than the tissue of interest, wherein the attenuation coefficient of everything other than the tissue of interest relates at least in part to light shunting through the sensor;
   determining a third value using the measurements provided to the controller and the first and second values, the third value representing an attenuation coefficient for the tissue of interest; and
   using the third value to calculate physiological parameters.

9. The method of claim 8, wherein using the sensor to take measurements of tissue of interest comprises:
  emitting electromagnetic radiation at tissue of interest using an emitter; and
  generating electrical signals corresponding to the amount of electromagnetic radiation detected by a detector.

10. The method of claim 8 wherein retrieving first and second values from memory comprises retrieving the first and second values from a memory in the sensor.

11. The method of claim 8 wherein retrieving first and second values from memory comprises retrieving the first and second values from a memory in the monitor.

12. The method of claim 11 comprising receiving coded values from the sensor and correlating the coded values with first and second values.

13. The method of claim 11 comprising recognizing the sensor and retrieving first and second values associated with the sensor.

14. The method of claim 8 wherein determining the third value comprises using the equation $$P_1 = \frac{I_{DET} - I_{LED}P_2}{I_{LED}},$$

wherein the first value is $I_{LED}$, the second value is $P_2$, the measured value is $I_{DET}$, and the third value is $P_1$ and wherein $I_{LED}$ represents the magnitude of the electromagnetic radiation emitted from the emitter, $I_{DET}$ represents the magnitude of the electromagnetic radiation detected by the detector, $P_2$ is the attenuation coefficient of everything but the tissue of interest, and $P_1$ is the attenuation coefficient of the tissue of interest.

* * * * *